US009028542B2

(12) United States Patent
Hill et al.

(10) Patent No.: US 9,028,542 B2
(45) Date of Patent: May 12, 2015

(54) VENOUS VALVE, SYSTEM, AND METHOD

(75) Inventors: Jason P. Hill, Cottage Grove, MN (US); Susan M. Shoemaker, Elk River, MN (US); Jaydeep Y. Kokate, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 168 days.

(21) Appl. No.: 13/226,172

(22) Filed: Sep. 6, 2011

(65) Prior Publication Data

US 2011/0319981 A1   Dec. 29, 2011

Related U.S. Application Data

(63) Continuation of application No. 11/150,331, filed on Jun. 10, 2005, now Pat. No. 8,012,198.

(51) Int. Cl.
*A61F 2/24* (2006.01)

(52) U.S. Cl.
CPC .............. *A61F 2/2418* (2013.01); *A61F 2/2412* (2013.01); *A61F 2/2475* (2013.01); *A61F 2250/0098* (2013.01); *A61F 2220/0016* (2013.01); *A61F 2220/005* (2013.01); *A61F 2220/0066* (2013.01); *A61F 2220/0075* (2013.01); *A61F 2230/0013* (2013.01)

(58) Field of Classification Search
CPC ....... A61F 2/24; A61F 2/2409; A61F 2/2418; A61F 2/2475; A61F 2/2412
USPC ........... 623/1.13, 1.14, 1.15, 1.16, 1.24, 1.26, 623/2.14, 2.16, 2.17, 2.18
See application file for complete search history.

(56) References Cited

U.S. PATENT DOCUMENTS

| | | | |
|---|---|---|---|
| 3,671,979 A | 6/1972 | Moulopoulos |
| 4,291,420 A | 9/1981 | Reul |
| 4,787,901 A | 11/1988 | Baykut |
| 4,872,874 A | 10/1989 | Taheri |
| 4,935,030 A | 6/1990 | Alonso |
| 4,994,077 A | 2/1991 | Dobben |
| 5,002,567 A | 3/1991 | Bona et al. |
| 5,141,491 A | 8/1992 | Bowald |
| 5,163,953 A | 11/1992 | Vince |
| 5,219,355 A | 6/1993 | Parodi et al. |
| 5,254,127 A | 10/1993 | Wholey et al. |
| 5,327,774 A | 7/1994 | Nguyen et al. |
| 5,332,402 A | 7/1994 | Teitelbaum |
| 5,370,685 A | 12/1994 | Stevens |

(Continued)

FOREIGN PATENT DOCUMENTS

| | | |
|---|---|---|
| EP | 0380666 | 8/1990 |
| EP | 0466518 | 1/1992 |

(Continued)

OTHER PUBLICATIONS

EP Communication pursuant to Article 94(3) EPC regarding related EP Application No. 06772822.0-1526.

(Continued)

*Primary Examiner* — David Isabella
*Assistant Examiner* — Suba Ganesan
(74) *Attorney, Agent, or Firm* — Vidas, Arrett & Steinkraus, P.A.

(57) ABSTRACT

A venous valve with a frame and a cover on the frame for unidirectional flow of a liquid through the valve.

17 Claims, 18 Drawing Sheets

(56) References Cited

U.S. PATENT DOCUMENTS

| | | |
|---|---|---|
| 5,411,552 A | 5/1995 | Andersen et al. |
| 5,469,868 A | 11/1995 | Reger |
| 5,480,423 A | 1/1996 | Ravenscroft et al. |
| 5,500,014 A | 3/1996 | Quijano et al. |
| 5,545,214 A | 8/1996 | Stevens |
| 5,554,185 A | 9/1996 | Block et al. |
| 5,643,208 A | 7/1997 | Parodi |
| 5,693,087 A | 12/1997 | Parodi |
| 5,713,953 A | 2/1998 | Vallana et al. |
| 5,716,370 A | 2/1998 | Williamson, IV et al. |
| 5,735,859 A | 4/1998 | Fischell et al. |
| 5,741,326 A | 4/1998 | Solovay |
| 5,741,333 A | 4/1998 | Frid |
| 5,800,506 A | 9/1998 | Perouse |
| 5,824,061 A | 10/1998 | Quijano et al. |
| 5,879,320 A | 3/1999 | Cazenave |
| 5,895,419 A | 4/1999 | Tweden et al. |
| 5,910,170 A | 6/1999 | Reimink et al. |
| 6,010,531 A | 1/2000 | Donlon et al. |
| 6,042,607 A | 3/2000 | Williamson, IV et al. |
| 6,139,575 A | 10/2000 | Shu et al. |
| 6,287,334 B1 | 9/2001 | Moll et al. |
| 6,312,447 B1 | 11/2001 | Grimes |
| 6,355,030 B1 | 3/2002 | Aldrich et al. |
| 6,402,780 B2 | 6/2002 | Williamson, IV et al. |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,451,054 B1 | 9/2002 | Stevens |
| 6,454,799 B1 | 9/2002 | Schreck |
| 6,461,366 B1 | 10/2002 | Seguin |
| 6,503,272 B2 | 1/2003 | Duerig et al. |
| 6,508,833 B2 | 1/2003 | Pavcnik et al. |
| 6,564,805 B2 | 5/2003 | Garrison et al. |
| 6,569,196 B1 | 5/2003 | Vesely |
| 6,602,286 B2 | 8/2003 | Strecker |
| 6,629,534 B1 | 10/2003 | St. Goar et al. |
| 6,635,085 B1 | 10/2003 | Caffey et al. |
| 6,666,885 B2 | 12/2003 | Moe |
| 6,666,886 B1 | 12/2003 | Tranquillo et al. |
| 6,669,725 B2 | 12/2003 | Scott |
| 6,673,109 B2 | 1/2004 | Cox |
| 6,676,698 B2 | 1/2004 | McGuckin, Jr. et al. |
| 6,676,702 B2 | 1/2004 | Mathis |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,692,512 B2 | 2/2004 | Jang |
| 6,695,866 B1 | 2/2004 | Kuehn et al. |
| 6,695,878 B2 | 2/2004 | McGuckin, Jr. et al. |
| 6,709,456 B2 | 3/2004 | Langberg et al. |
| 6,709,457 B1 | 3/2004 | Otte et al. |
| 6,716,241 B2 | 4/2004 | Wilder et al. |
| 6,716,244 B2 | 4/2004 | Klaco |
| 6,719,767 B1 | 4/2004 | Kimblad |
| 6,719,784 B2 | 4/2004 | Henderson |
| 6,719,786 B2 | 4/2004 | Ryan et al. |
| 6,719,787 B2 | 4/2004 | Cox |
| 6,719,788 B2 | 4/2004 | Cox |
| 6,719,789 B2 | 4/2004 | Cox |
| 6,719,790 B2 | 4/2004 | Brendzel et al. |
| 6,723,038 B1 | 4/2004 | Schroeder et al. |
| 6,723,122 B2 | 4/2004 | Yang et al. |
| 6,723,123 B1 | 4/2004 | Kazatchkov et al. |
| 6,726,715 B2 | 4/2004 | Sutherland |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,730,122 B1 | 5/2004 | Pan et al. |
| 6,736,845 B2 | 5/2004 | Marquez et al. |
| 6,736,846 B2 | 5/2004 | Cox |
| 6,749,630 B2 | 6/2004 | McCarthy et al. |
| 6,752,813 B2 | 6/2004 | Goldfarb et al. |
| 6,752,828 B2 | 6/2004 | Thornton |
| 6,755,857 B2 | 6/2004 | Peterson et al. |
| 6,761,734 B2 | 7/2004 | Suhr |
| 6,761,735 B2 | 7/2004 | Eberhardt et al. |
| 6,764,494 B2 | 7/2004 | Menz et al. |
| 6,764,508 B1 | 7/2004 | Roehe et al. |
| 6,764,509 B2 | 7/2004 | Chinn et al. |
| 6,764,510 B2 | 7/2004 | Vidlund et al. |
| 6,767,362 B2 | 7/2004 | Schreck |
| 6,770,083 B2 | 8/2004 | Seguin |
| 6,780,200 B2 | 8/2004 | Jansen |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,231 B2 | 9/2004 | Liddicoat et al. |
| 6,793,673 B2 | 9/2004 | Kowalsky et al. |
| 6,797,000 B2 | 9/2004 | Simpson et al. |
| 6,797,001 B2 | 9/2004 | Mathis et al. |
| 6,797,002 B2 | 9/2004 | Spence et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,830,584 B1 | 12/2004 | Seguin |
| 6,830,585 B1 | 12/2004 | Artof et al. |
| 6,837,902 B2 | 1/2005 | Nguyen et al. |
| 6,840,246 B2 | 1/2005 | Downing |
| 6,840,957 B2 | 1/2005 | DiMatteo et al. |
| 6,846,324 B2 | 1/2005 | Stobie |
| 6,846,325 B2 | 1/2005 | Liddicoat |
| 6,858,039 B2 | 2/2005 | McCarthy |
| 6,869,444 B2 | 3/2005 | Gabbay |
| 6,872,226 B2 | 3/2005 | Cali et al. |
| 6,875,224 B2 | 4/2005 | Grimes |
| 6,875,230 B1 | 4/2005 | Morita et al. |
| 6,875,231 B2 | 4/2005 | Anduiza et al. |
| 6,881,199 B2 | 4/2005 | Wilk et al. |
| 6,881,224 B2 | 4/2005 | Kruse et al. |
| 6,883,522 B2 | 4/2005 | Spence et al. |
| 6,890,352 B1 | 5/2005 | Lentell |
| 6,890,353 B2 | 5/2005 | Cohn et al. |
| 6,893,459 B1 | 5/2005 | Macoviak |
| 6,893,460 B2 | 5/2005 | Spenser et al. |
| 6,896,700 B2 | 5/2005 | Lu et al. |
| 6,902,576 B2 | 6/2005 | Drasler et al. |
| 6,908,478 B2 | 6/2005 | Alferness et al. |
| 6,908,481 B2 | 6/2005 | Cribier |
| 6,911,043 B2 | 6/2005 | Myers et al. |
| 6,913,608 B2 | 7/2005 | Liddicoat et al. |
| 6,916,338 B2 | 7/2005 | Speziali |
| 6,918,917 B1 | 7/2005 | Nguyen et al. |
| 6,921,407 B2 | 7/2005 | Nguyen et al. |
| 6,921,811 B2 | 7/2005 | Zamora et al. |
| 6,926,715 B1 | 8/2005 | Hauck et al. |
| 6,926,730 B1 | 8/2005 | Nguyen et al. |
| 6,929,653 B2 | 8/2005 | Strecter |
| 6,932,838 B2 | 8/2005 | Schwartz et al. |
| 6,936,067 B2 | 8/2005 | Buchanan |
| 6,939,359 B2 | 9/2005 | Tu et al. |
| 6,942,694 B2 | 9/2005 | Liddicoat et al. |
| 6,945,957 B2 | 9/2005 | Freyman |
| 6,945,978 B1 | 9/2005 | Hyde |
| 6,945,996 B2 | 9/2005 | Sedransk |
| 6,945,997 B2 | 9/2005 | Huynh et al. |
| 6,949,122 B2 | 9/2005 | Adams et al. |
| 6,951,571 B1 | 10/2005 | Srivastava |
| 6,951,573 B1 | 10/2005 | Dilling |
| 6,953,332 B1 | 10/2005 | Kurk et al. |
| 6,955,689 B2 | 10/2005 | Ryan et al. |
| 6,958,076 B2 | 10/2005 | Acosta et al. |
| 6,962,605 B2 | 11/2005 | Cosgrove et al. |
| 6,964,682 B2 | 11/2005 | Nguyen-Thien-Nhon et al. |
| 6,964,683 B2 | 11/2005 | Kowalsky et al. |
| 6,964,684 B2 | 11/2005 | Ortiz et al. |
| 6,966,925 B2 | 11/2005 | Stobie |
| 6,966,926 B2 | 11/2005 | Mathis |
| 6,974,464 B2 | 12/2005 | Quijano et al. |

(56) References Cited

U.S. PATENT DOCUMENTS

| | | |
|---|---|---|
| 6,974,474 B2 | 12/2005 | Pavcnik et al. |
| 6,974,476 B2 | 12/2005 | McGuckin, Jr. et al. |
| 6,976,995 B2 | 12/2005 | Mathis et al. |
| 6,979,350 B2 | 12/2005 | Moll et al. |
| 6,986,775 B2 | 1/2006 | Morales et al. |
| 6,989,027 B2 | 1/2006 | Allen et al. |
| 6,989,028 B2 | 1/2006 | Lashinski et al. |
| 6,997,950 B2 | 2/2006 | Chawla |
| 6,997,951 B2 | 2/2006 | Solem et al. |
| 7,004,176 B2 | 2/2006 | Lau |
| 7,007,396 B2 | 3/2006 | Rudko et al. |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,018,407 B1 | 3/2006 | Wright et al. |
| 7,018,408 B2 | 3/2006 | Bailey et al. |
| 7,022,134 B1 | 4/2006 | Quijano et al. |
| 7,025,780 B2 | 4/2006 | Gabbay |
| 7,033,390 B2 | 4/2006 | Johnson et al. |
| 7,037,333 B2 | 5/2006 | Myers et al. |
| 7,037,334 B1 | 5/2006 | Hlavka et al. |
| 7,041,128 B2 | 5/2006 | Mcguckin, Jr. et al. |
| 7,041,132 B2 | 5/2006 | Quijano et al. |
| 7,044,966 B2 | 5/2006 | Svanidze et al. |
| 7,044,967 B1 | 5/2006 | Solem et al. |
| 7,048,754 B2 | 5/2006 | Martin et al. |
| 7,048,757 B2 | 5/2006 | Shaknovich |
| 7,052,487 B2 | 5/2006 | Cohn et al. |
| 7,052,507 B2 | 5/2006 | Wakuda et al. |
| 7,063,722 B2 | 6/2006 | Marquez |
| 7,066,954 B2 | 6/2006 | Ryan |
| 7,070,616 B2 | 7/2006 | Majercak et al. |
| 7,070,618 B2 | 7/2006 | Streeter |
| 7,077,862 B2 | 7/2006 | Vidlund et al. |
| 7,081,131 B2 | 7/2006 | Thornton |
| 7,087,064 B1 | 8/2006 | Hyde |
| 7,089,051 B2 | 8/2006 | Javerud et al. |
| 7,090,695 B2 | 8/2006 | Solem et al. |
| 7,267,686 B2 | 9/2007 | DiMatteo et al. |
| 7,867,274 B2 | 1/2011 | Hill et al. |
| 8,221,492 B2 * | 7/2012 | Case et al. .................. 623/1.24 |
| 2001/0010017 A1 | 7/2001 | Letac et al. |
| 2001/0039450 A1 | 11/2001 | Pavcnik et al. |
| 2002/0013571 A1 | 1/2002 | Goldfarb et al. |
| 2002/0026216 A1 | 2/2002 | Grimes |
| 2002/0082630 A1 | 6/2002 | Menz et al. |
| 2002/0107565 A1 | 8/2002 | Greenhalgh |
| 2002/0123802 A1 | 9/2002 | Snyders |
| 2002/0138135 A1 | 9/2002 | Duerig et al. |
| 2002/0151970 A1 | 10/2002 | Garrison et al. |
| 2002/0183835 A1 | 12/2002 | Taylor et al. |
| 2002/0183838 A1 | 12/2002 | Liddicoat et al. |
| 2002/0198594 A1 | 12/2002 | Schreck |
| 2003/0050694 A1 | 3/2003 | Yang et al. |
| 2003/0130729 A1 | 7/2003 | Paniagua et al. |
| 2003/0149477 A1 | 8/2003 | Gabbay |
| 2003/0163194 A1 | 8/2003 | Quijano et al. |
| 2003/0167071 A1 | 9/2003 | Martin |
| 2003/0171806 A1 | 9/2003 | Mathis et al. |
| 2003/0199975 A1 | 10/2003 | Gabbay |
| 2003/0229394 A1 | 12/2003 | Ogle et al. |
| 2003/0229395 A1 | 12/2003 | Cox |
| 2003/0233142 A1 | 12/2003 | Morales et al. |
| 2003/0236568 A1 | 12/2003 | Hojeibane et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015230 A1 | 1/2004 | Moll et al. |
| 2004/0015232 A1 | 1/2004 | Shu et al. |
| 2004/0015233 A1 | 1/2004 | Jansen |
| 2004/0019374 A1 | 1/2004 | Hojeibane et al. |
| 2004/0019377 A1 | 1/2004 | Taylor et al. |
| 2004/0019378 A1 | 1/2004 | Hlavka et al. |
| 2004/0024447 A1 | 2/2004 | Haverich |
| 2004/0024451 A1 | 2/2004 | Johnson et al. |
| 2004/0024452 A1 | 2/2004 | Kruse et al. |
| 2004/0030321 A1 | 2/2004 | Fangrow, Jr. |
| 2004/0030381 A1 | 2/2004 | Shu |
| 2004/0030382 A1 | 2/2004 | St. Goar et al. |
| 2004/0030405 A1 | 2/2004 | Carpentier et al. |
| 2004/0034380 A1 | 2/2004 | Woolfson et al. |
| 2004/0034408 A1 | 2/2004 | Majercak et al. |
| 2004/0034411 A1 | 2/2004 | Quijano et al. |
| 2004/0039436 A1 | 2/2004 | Spenser et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0044403 A1 | 3/2004 | Bischoff et al. |
| 2004/0049207 A1 | 3/2004 | Goldfarb et al. |
| 2004/0049211 A1 | 3/2004 | Tremulis et al. |
| 2004/0049266 A1 | 3/2004 | Anduiza et al. |
| 2004/0059351 A1 | 3/2004 | Eigler et al. |
| 2004/0059411 A1 | 3/2004 | Strecker |
| 2004/0059412 A1 | 3/2004 | Lytle, IV et al. |
| 2004/0060161 A1 | 4/2004 | Leal et al. |
| 2004/0073301 A1 | 4/2004 | Donlon et al. |
| 2004/0073302 A1 | 4/2004 | Rourke et al. |
| 2004/0078072 A1 | 4/2004 | Tu et al. |
| 2004/0078074 A1 | 4/2004 | Anderson et al. |
| 2004/0082910 A1 | 4/2004 | Constantz et al. |
| 2004/0082923 A1 | 4/2004 | Field |
| 2004/0082991 A1 | 4/2004 | Nguyen et al. |
| 2004/0087975 A1 | 5/2004 | Lucatero et al. |
| 2004/0088045 A1 | 5/2004 | Cox |
| 2004/0088046 A1 | 5/2004 | Speziali |
| 2004/0092858 A1 | 5/2004 | Wilson et al. |
| 2004/0093060 A1 | 5/2004 | Seguin et al. |
| 2004/0093070 A1 | 5/2004 | Hojeibane et al. |
| 2004/0093080 A1 | 5/2004 | Helmus |
| 2004/0097979 A1 | 5/2004 | Svanidze et al. |
| 2004/0098098 A1 | 5/2004 | McGuckin, Jr. et al. |
| 2004/0098112 A1 | 5/2004 | DiMatteo et al. |
| 2004/0102839 A1 | 5/2004 | Cohn et al. |
| 2004/0102840 A1 | 5/2004 | Solem et al. |
| 2004/0102842 A1 | 5/2004 | Jansen |
| 2004/0106976 A1 | 6/2004 | Bailey et al. |
| 2004/0106990 A1 | 6/2004 | Spence et al. |
| 2004/0106991 A1 | 6/2004 | Hopkins et al. |
| 2004/0111096 A1 | 6/2004 | Tu et al. |
| 2004/0117009 A1 | 6/2004 | Cali et al. |
| 2004/0122448 A1 | 6/2004 | Levine |
| 2004/0122512 A1 | 6/2004 | Navia et al. |
| 2004/0122513 A1 | 6/2004 | Navia et al. |
| 2004/0122514 A1 | 6/2004 | Fogarty et al. |
| 2004/0122515 A1 | 6/2004 | Chu |
| 2004/0122516 A1 | 6/2004 | Fogarty et al. |
| 2004/0127979 A1 | 7/2004 | Wilson et al. |
| 2004/0127980 A1 | 7/2004 | Kowalsky et al. |
| 2004/0127981 A1 | 7/2004 | Randert et al. |
| 2004/0127982 A1 | 7/2004 | Machold et al. |
| 2004/0133220 A1 | 7/2004 | Lashinski et al. |
| 2004/0133267 A1 | 7/2004 | Lane |
| 2004/0133273 A1 | 7/2004 | Cox |
| 2004/0138742 A1 | 7/2004 | Myers et al. |
| 2004/0138743 A1 | 7/2004 | Myers et al. |
| 2004/0138744 A1 | 7/2004 | Lashinski et al. |
| 2004/0138745 A1 | 7/2004 | Macoviak et al. |
| 2004/0148018 A1 | 7/2004 | Carpentier et al. |
| 2004/0148019 A1 | 7/2004 | Vidlund et al. |
| 2004/0148020 A1 | 7/2004 | Vidlund et al. |
| 2004/0153052 A1 | 8/2004 | Mathis |
| 2004/0153146 A1 | 8/2004 | Lashinski et al. |
| 2004/0153147 A1 | 8/2004 | Mathis |
| 2004/0158321 A1 | 8/2004 | Reuter et al. |
| 2004/0162610 A1 | 8/2004 | Liska et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0176839 A1 | 9/2004 | Huynh et al. |
| 2004/0176840 A1 | 9/2004 | Langberg et al. |
| 2004/0181238 A1 | 9/2004 | Zarbatany et al. |

(56) References Cited

U.S. PATENT DOCUMENTS

| | | |
|---|---|---|
| 2004/0186444 A1 | 9/2004 | Daly et al. |
| 2004/0186558 A1* | 9/2004 | Pavcnik et al. ............... 623/1.24 |
| 2004/0186561 A1 | 9/2004 | Mcguckin, Jr. et al. |
| 2004/0186563 A1 | 9/2004 | Lobbi |
| 2004/0186565 A1 | 9/2004 | Schreck |
| 2004/0186566 A1 | 9/2004 | Hindrichs et al. |
| 2004/0193191 A1 | 9/2004 | Starksen et al. |
| 2004/0193253 A1 | 9/2004 | Thorpe et al. |
| 2004/0193260 A1 | 9/2004 | Alferness et al. |
| 2004/0199155 A1 | 10/2004 | Mollenauer |
| 2004/0199183 A1 | 10/2004 | Oz et al. |
| 2004/0199191 A1 | 10/2004 | Schwartz |
| 2004/0204758 A1 | 10/2004 | Eberhardt et al. |
| 2004/0206363 A1 | 10/2004 | Mccarthy et al. |
| 2004/0210240 A1 | 10/2004 | Saint |
| 2004/0210301 A1 | 10/2004 | Obermiller |
| 2004/0210303 A1 | 10/2004 | Sedransk |
| 2004/0210304 A1 | 10/2004 | Seguin et al. |
| 2004/0210305 A1 | 10/2004 | Shu et al. |
| 2004/0210306 A1 | 10/2004 | Quijano et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0220654 A1 | 11/2004 | Mathis et al. |
| 2004/0220657 A1 | 11/2004 | Nieminen et al. |
| 2004/0225322 A1 | 11/2004 | Garrison et al. |
| 2004/0225344 A1 | 11/2004 | Hoffa et al. |
| 2004/0225348 A1 | 11/2004 | Case et al. |
| 2004/0225352 A1 | 11/2004 | Osborne et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0230117 A1 | 11/2004 | Tosaya et al. |
| 2004/0230297 A1 | 11/2004 | Thornton |
| 2004/0236411 A1 | 11/2004 | Sarac et al. |
| 2004/0236418 A1 | 11/2004 | Stevens |
| 2004/0236419 A1 | 11/2004 | Milo |
| 2004/0243153 A1 | 12/2004 | Liddicoat et al. |
| 2004/0243219 A1 | 12/2004 | Fischer et al. |
| 2004/0243227 A1 | 12/2004 | Starksen et al. |
| 2004/0243228 A1 | 12/2004 | Kowalsky et al. |
| 2004/0243230 A1 | 12/2004 | Navia et al. |
| 2004/0254600 A1 | 12/2004 | Zarbatany et al. |
| 2004/0254636 A1 | 12/2004 | Flagle et al. |
| 2004/0260276 A1 | 12/2004 | Rudko et al. |
| 2004/0260317 A1 | 12/2004 | Bloom et al. |
| 2004/0260322 A1 | 12/2004 | Rudko et al. |
| 2004/0260389 A1 | 12/2004 | Case et al. |
| 2004/0260390 A1 | 12/2004 | Sarac et al. |
| 2004/0260393 A1 | 12/2004 | Randert et al. |
| 2004/0260394 A1 | 12/2004 | Douk et al. |
| 2004/0267357 A1 | 12/2004 | Allen et al. |
| 2005/0004583 A1 | 1/2005 | Oz et al. |
| 2005/0004667 A1 | 1/2005 | Swinford et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021056 A1 | 1/2005 | St. Goar et al. |
| 2005/0021136 A1 | 1/2005 | Xie et al. |
| 2005/0027261 A1 | 2/2005 | Weaver et al. |
| 2005/0027348 A1 | 2/2005 | Case et al. |
| 2005/0027351 A1 | 2/2005 | Reuter et al. |
| 2005/0027353 A1 | 2/2005 | Alferness et al. |
| 2005/0033398 A1 | 2/2005 | Seguin |
| 2005/0033419 A1 | 2/2005 | Alferness et al. |
| 2005/0033446 A1 | 2/2005 | Deem et al. |
| 2005/0038506 A1 | 2/2005 | Webler et al. |
| 2005/0038507 A1 | 2/2005 | Alferness et al. |
| 2005/0043790 A1 | 2/2005 | Seguin |
| 2005/0043792 A1 | 2/2005 | Solem |
| 2005/0049679 A1 | 3/2005 | Taylor et al. |
| 2005/0049692 A1 | 3/2005 | Numamoto et al. |
| 2005/0049696 A1 | 3/2005 | Siess et al. |
| 2005/0049697 A1 | 3/2005 | Sievers |
| 2005/0054977 A1 | 3/2005 | Laird et al. |
| 2005/0055079 A1 | 3/2005 | Duran |
| 2005/0055087 A1 | 3/2005 | Starksen |
| 2005/0055088 A1 | 3/2005 | Liddicoat et al. |
| 2005/0055089 A1 | 3/2005 | Macoviak et al. |
| 2005/0060029 A1 | 3/2005 | Le et al. |
| 2005/0060030 A1 | 3/2005 | Lashinski et al. |
| 2005/0065460 A1 | 3/2005 | Laird |
| 2005/0065550 A1 | 3/2005 | Starksen et al. |
| 2005/0065594 A1 | 3/2005 | DiMatteo et al. |
| 2005/0065597 A1 | 3/2005 | Lansac |
| 2005/0070998 A1 | 3/2005 | Rourke et al. |
| 2005/0075584 A1 | 4/2005 | Cali |
| 2005/0075659 A1 | 4/2005 | Realyvasquez et al. |
| 2005/0075662 A1 | 4/2005 | Pedersen et al. |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075723 A1 | 4/2005 | Schroeder et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080483 A1 | 4/2005 | Solem et al. |
| 2005/0085900 A1 | 4/2005 | Case et al. |
| 2005/0085903 A1 | 4/2005 | Lau |
| 2005/0085904 A1 | 4/2005 | Lemmon |
| 2005/0090846 A1 | 4/2005 | Pedersen et al. |
| 2005/0096735 A1 | 5/2005 | Hojeibane et al. |
| 2005/0096738 A1 | 5/2005 | Cali et al. |
| 2005/0096739 A1 | 5/2005 | Cao |
| 2005/0096740 A1 | 5/2005 | Langberg et al. |
| 2005/0101975 A1 | 5/2005 | Nguyen et al. |
| 2005/0102026 A1 | 5/2005 | Turner et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107872 A1 | 5/2005 | Mensah et al. |
| 2005/0113910 A1 | 5/2005 | Paniagua et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137676 A1 | 6/2005 | Richardson et al. |
| 2005/0137681 A1 | 6/2005 | Shoemaker et al. |
| 2005/0137682 A1 | 6/2005 | Justin |
| 2005/0137685 A1 | 6/2005 | Nieminen et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0143810 A1 | 6/2005 | Dauner et al. |
| 2005/0143811 A1 | 6/2005 | Realyvasquez |
| 2005/0149014 A1 | 7/2005 | Hauck et al. |
| 2005/0149179 A1 | 7/2005 | Mathis et al. |
| 2005/0149180 A1 | 7/2005 | Mathis et al. |

(56) References Cited

U.S. PATENT DOCUMENTS

| | | |
|---|---|---|
| 2005/0149181 A1 | 7/2005 | Eberhardt |
| 2005/0159810 A1 | 7/2005 | Filsoufi |
| 2005/0159811 A1 | 7/2005 | Lane |
| 2005/0165477 A1 | 7/2005 | Anduiza et al. |
| 2005/0165478 A1 | 7/2005 | Song |
| 2005/0171472 A1 | 8/2005 | Lutter |
| 2005/0171601 A1 | 8/2005 | Cosgrove et al. |
| 2005/0177227 A1 | 8/2005 | Heim et al. |
| 2005/0177228 A1 | 8/2005 | Solem et al. |
| 2005/0182483 A1 | 8/2005 | Osborne et al. |
| 2005/0184122 A1 | 8/2005 | Hlavka et al. |
| 2005/0187614 A1 | 8/2005 | Agnew |
| 2005/0187616 A1 | 8/2005 | Realyvasquez |
| 2005/0187617 A1 | 8/2005 | Navia |
| 2005/0192606 A1 | 9/2005 | Paul, Jr. et al. |
| 2005/0192665 A1 | 9/2005 | Spenser et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216039 A1 | 9/2005 | Lederman |
| 2005/0216077 A1 | 9/2005 | Mathis et al. |
| 2005/0216078 A1 | 9/2005 | Starksen et al. |
| 2005/0222675 A1 | 10/2005 | Sauter |
| 2005/0222678 A1 | 10/2005 | Lashinski et al. |
| 2005/0228422 A1 | 10/2005 | Machold et al. |
| 2005/0228479 A1 | 10/2005 | Pavcnik et al. |
| 2005/0228486 A1 | 10/2005 | Case et al. |
| 2005/0228494 A1 | 10/2005 | Marquez |
| 2005/0228495 A1 | 10/2005 | Macoviak |
| 2005/0228496 A1 | 10/2005 | Mensah et al. |
| 2005/0234541 A1 | 10/2005 | Hunt et al. |
| 2005/0234546 A1 | 10/2005 | Nugent et al. |
| 2005/0240200 A1 | 10/2005 | Bergheim |
| 2005/0240202 A1 | 10/2005 | Shennib et al. |
| 2005/0240255 A1 | 10/2005 | Schaeffer |
| 2005/0240259 A1 | 10/2005 | Sisken et al. |
| 2005/0240262 A1 | 10/2005 | White |
| 2005/0244460 A1 | 11/2005 | Alferiev et al. |
| 2005/0246013 A1 | 11/2005 | Gabbay |
| 2005/0251251 A1 | 11/2005 | Cribier |
| 2005/0256566 A1 | 11/2005 | Gabbay |
| 2005/0261704 A1 | 11/2005 | Mathis |
| 2005/0261759 A1 | 11/2005 | Lambrecht et al. |
| 2005/0267493 A1 | 12/2005 | Schreck et al. |
| 2005/0267560 A1 | 12/2005 | Bates |
| 2005/0267565 A1 | 12/2005 | Dave et al. |
| 2005/0267571 A1 | 12/2005 | Spence et al. |
| 2005/0267573 A9 | 12/2005 | Macoviak et al. |
| 2005/0267574 A1 | 12/2005 | Cohn et al. |
| 2005/0272969 A1 | 12/2005 | Alferness et al. |
| 2005/0273160 A1 | 12/2005 | Lashinski et al. |
| 2005/0278015 A1 | 12/2005 | Dave et al. |
| 2005/0283178 A1 | 12/2005 | Flagle et al. |
| 2005/0288779 A1 | 12/2005 | Shaoulian et al. |
| 2006/0000715 A1 | 1/2006 | Whitcher et al. |
| 2006/0002075 A1 | 1/2006 | Wei-Chieh |
| 2006/0004439 A1 | 1/2006 | Spenser et al. |
| 2006/0004442 A1 | 1/2006 | Spenser et al. |
| 2006/0009804 A1 | 1/2006 | Pederson |
| 2006/0009841 A1 | 1/2006 | Mcguckin, Jr. et al. |
| 2006/0009842 A1 | 1/2006 | Huynh et al. |
| 2006/0013805 A1 | 1/2006 | Hebbel et al. |
| 2006/0013855 A1 | 1/2006 | Carpenter et al. |
| 2006/0015136 A1 | 1/2006 | Besselink |
| 2006/0015178 A1 | 1/2006 | Moaddeb et al. |
| 2006/0015179 A1 | 1/2006 | Bulman-Fleming et al. |
| 2006/0020327 A1 | 1/2006 | Lashinski et al. |
| 2006/0020332 A1 | 1/2006 | Lashinski et al. |
| 2006/0020334 A1 | 1/2006 | Lashinski et al. |
| 2006/0020335 A1 | 1/2006 | Kowalsky et al. |
| 2006/0020336 A1 | 1/2006 | Liddicoat |
| 2006/0025750 A1 | 2/2006 | Startksen et al. |
| 2006/0025784 A1 | 2/2006 | Startksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0025856 A1 | 2/2006 | Ryan et al. |
| 2006/0025857 A1 | 2/2006 | Bergheim et al. |
| 2006/0030747 A1 | 2/2006 | Kantrowitz et al. |
| 2006/0030866 A1 | 2/2006 | Schreck |
| 2006/0030882 A1 | 2/2006 | Adams et al. |
| 2006/0030885 A1 | 2/2006 | Hyde |
| 2006/0036317 A1 | 2/2006 | Vidlund et al. |
| 2006/0041305 A1 | 2/2006 | Lauterjung |
| 2006/0041306 A1 | 2/2006 | Vidlund et al. |
| 2006/0047297 A1 | 3/2006 | Case |
| 2006/0047338 A1 | 3/2006 | Jenson |
| 2006/0047343 A1 | 3/2006 | Oviatt et al. |
| 2006/0052804 A1 | 3/2006 | Mialhe |
| 2006/0052867 A1 | 3/2006 | Revuelta et al. |
| 2006/0058817 A1 | 3/2006 | Starksen et al. |
| 2006/0058865 A1 | 3/2006 | Case et al. |
| 2006/0058871 A1 | 3/2006 | Zakay et al. |
| 2006/0058889 A1 | 3/2006 | Case et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0064174 A1 | 3/2006 | Zadno |
| 2006/0069400 A1 | 3/2006 | Burnett et al. |
| 2006/0069429 A1 | 3/2006 | Spence et al. |
| 2006/0069430 A9 | 3/2006 | Randert et al. |
| 2006/0074483 A1 | 4/2006 | Schrayer |
| 2006/0074484 A1 | 4/2006 | Huber |
| 2006/0074485 A1 | 4/2006 | Realyvasquez |
| 2006/0085060 A1 | 4/2006 | Campbell |
| 2006/0089708 A1 | 4/2006 | Osse et al. |
| 2006/0095115 A1 | 5/2006 | Bladilah et al. |
| 2006/0095125 A1 | 5/2006 | Chinn et al. |
| 2006/0099326 A1 | 5/2006 | Keogh et al. |
| 2006/0100697 A1 | 5/2006 | Casanova |
| 2006/0100699 A1 | 5/2006 | Vidlund et al. |
| 2006/0106278 A1 | 5/2006 | Machold et al. |
| 2006/0106279 A1 | 5/2006 | Machold et al. |
| 2006/0106456 A9 | 5/2006 | Machold et al. |
| 2006/0111660 A1 | 5/2006 | Wolf et al. |
| 2006/0111773 A1 | 5/2006 | Rittgers et al. |
| 2006/0111774 A1 | 5/2006 | Samkov et al. |
| 2006/0116572 A1 | 6/2006 | Case |
| 2006/0116756 A1 | 6/2006 | Solem et al. |
| 2006/0122686 A1 | 6/2006 | Gilad et al. |
| 2006/0122692 A1 | 6/2006 | Gilad et al. |
| 2006/0122693 A1 | 6/2006 | Biadillah et al. |
| 2006/0127443 A1 | 6/2006 | Helmus |
| 2006/0129235 A1 | 6/2006 | Seguin et al. |
| 2006/0129236 A1 | 6/2006 | Mccarthy |
| 2006/0135476 A1 | 6/2006 | Kutryk et al. |
| 2006/0135964 A1 | 6/2006 | Vesely |
| 2006/0135967 A1 | 6/2006 | Realyvasquez |
| 2006/0136044 A1 | 6/2006 | Osborne |
| 2006/0136045 A1 | 6/2006 | Flagle et al. |
| 2006/0136052 A1 | 6/2006 | Vesely |
| 2006/0136054 A1 | 6/2006 | Berg et al. |
| 2006/0142846 A1 | 6/2006 | Pavcnik et al. |
| 2006/0142847 A1 | 6/2006 | Shaknovich |
| 2006/0142848 A1 | 6/2006 | Gabbay |
| 2006/0142854 A1 | 6/2006 | Alferness et al. |
| 2006/0149358 A1 | 7/2006 | Zilla et al. |
| 2006/0149360 A1 | 7/2006 | Schwammenthal et al. |
| 2006/0149367 A1 | 7/2006 | Sieracki |
| 2006/0149368 A1 | 7/2006 | Spence |
| 2006/0161133 A1 | 7/2006 | Laird et al. |
| 2006/0161248 A1 | 7/2006 | Case et al. |
| 2006/0161249 A1 | 7/2006 | Realyvasquez et al. |
| 2006/0161250 A1 | 7/2006 | Shaw |
| 2006/0167468 A1 | 7/2006 | Gabbay |
| 2006/0167541 A1 | 7/2006 | Lattouf |

(56) References Cited

U.S. PATENT DOCUMENTS

| | | |
|---|---|---|
| 2006/0167542 A1 | 7/2006 | Quintessenza |
| 2006/0190074 A1 | 8/2006 | Hill |
| 2011/0071625 A1 | 3/2011 | Hill et al. |

FOREIGN PATENT DOCUMENTS

| | | |
|---|---|---|
| FR | 2728457 | 6/1996 |
| WO | 8800459 | 1/1988 |
| WO | 9015582 | 12/1990 |
| WO | 9501669 | 1/1995 |
| WO | 9619159 | 6/1996 |
| WO | 9803656 | 1/1998 |
| WO | 9846115 | 10/1998 |
| WO | 9904724 | 2/1999 |
| WO | 0067679 | 11/2000 |
| WO | 0115650 | 3/2001 |
| WO | 0117462 | 3/2001 |
| WO | 0128459 | 4/2001 |
| WO | 0149213 | 7/2001 |
| WO | 03047468 | 6/2003 |
| WO | 03084443 | 10/2003 |
| WO | 2004019825 | 3/2004 |
| WO | 2004021893 | 3/2004 |
| WO | 2004023980 | 3/2004 |
| WO | 2004030568 | 4/2004 |
| WO | 2004030569 | 4/2004 |
| WO | 2004030570 | 4/2004 |
| WO | 2004032724 | 4/2004 |
| WO | 2004032796 | 4/2004 |
| WO | 2004037128 | 5/2004 |
| WO | 2004037317 | 5/2004 |
| WO | 2004039432 | 5/2004 |
| WO | 2004043265 | 5/2004 |
| WO | 2004043273 | 5/2004 |
| WO | 2004043293 | 5/2004 |
| WO | 2004045370 | 6/2004 |
| WO | 2004045378 | 6/2004 |
| WO | 2004045463 | 6/2004 |
| WO | 2004047677 | 6/2004 |
| WO | 2004060217 | 7/2004 |
| WO | 2004060470 | 7/2004 |
| WO | 2004062725 | 7/2004 |
| WO | 2004066803 | 8/2004 |
| WO | 2004066826 | 8/2004 |
| WO | 2004069287 | 8/2004 |
| WO | 2004075789 | 9/2004 |
| WO | 2004080352 | 9/2004 |
| WO | 2004082523 | 9/2004 |
| WO | 2004082527 | 9/2004 |
| WO | 2004082528 | 9/2004 |
| WO | 2004082536 | 9/2004 |
| WO | 2004082537 | 9/2004 |
| WO | 2004082538 | 9/2004 |
| WO | 2004082757 | 9/2004 |
| WO | 2004084746 | 10/2004 |
| WO | 2004084770 | 10/2004 |
| WO | 2004089246 | 10/2004 |
| WO | 2004089250 | 10/2004 |
| WO | 2004089253 | 10/2004 |
| WO | 2004091449 | 10/2004 |
| WO | 2004091454 | 10/2004 |
| WO | 2004093638 | 11/2004 |
| WO | 2004093726 | 11/2004 |
| WO | 2004093728 | 11/2004 |
| WO | 2004093730 | 11/2004 |
| WO | 2004093745 | 11/2004 |
| WO | 2004093935 | 11/2004 |
| WO | 2004096100 | 11/2004 |
| WO | 2004103222 | 12/2004 |
| WO | 2004103223 | 12/2004 |
| WO | 2004105584 | 12/2004 |
| WO | 2004105651 | 12/2004 |
| WO | 2004112582 | 12/2004 |
| WO | 2004112585 | 12/2004 |
| WO | 2004112643 | 12/2004 |
| WO | 2004112652 | 12/2004 |
| WO | 2004112657 | 12/2004 |
| WO | 2004112658 | 12/2004 |
| WO | 2005000152 | 1/2005 |
| WO | 2005002424 | 1/2005 |
| WO | 2005002466 | 1/2005 |
| WO | 2005004753 | 1/2005 |
| WO | 2005007017 | 1/2005 |
| WO | 2005007018 | 1/2005 |
| WO | 2005007036 | 1/2005 |
| WO | 2005007037 | 1/2005 |
| WO | 2005009285 | 2/2005 |
| WO | 2005009286 | 2/2005 |
| WO | 2005009505 | 2/2005 |
| WO | 2005009506 | 2/2005 |
| WO | 2005011473 | 2/2005 |
| WO | 2005011534 | 2/2005 |
| WO | 2005011535 | 2/2005 |
| WO | 2005013860 | 2/2005 |
| WO | 2005018507 | 3/2005 |
| WO | 2005021063 | 3/2005 |
| WO | 2005023155 | 3/2005 |
| WO | 2005025644 | 3/2005 |
| WO | 2005027790 | 3/2005 |
| WO | 2005027797 | 3/2005 |
| WO | 2005034812 | 4/2005 |
| WO | 2005039428 | 5/2005 |
| WO | 2005039452 | 5/2005 |
| WO | 2005046488 | 5/2005 |
| WO | 2005046528 | 5/2005 |
| WO | 2005046529 | 5/2005 |
| WO | 2005046530 | 5/2005 |
| WO | 2005046531 | 5/2005 |
| WO | 2005048883 | 6/2005 |
| WO | 2005049103 | 6/2005 |
| WO | 2005051226 | 6/2005 |
| WO | 2005055811 | 6/2005 |
| WO | 2005055883 | 6/2005 |
| WO | 2005058206 | 6/2005 |
| WO | 2005065585 | 7/2005 |
| WO | 2005065593 | 7/2005 |
| WO | 2005065594 | 7/2005 |
| WO | 2005070342 | 8/2005 |
| WO | 2005070343 | 8/2005 |
| WO | 2005072654 | 8/2005 |
| WO | 2005072655 | 8/2005 |
| WO | 2005079706 | 9/2005 |
| WO | 2005082288 | 9/2005 |
| WO | 2005082289 | 9/2005 |
| WO | 2005084595 | 9/2005 |
| WO | 2005087139 | 9/2005 |
| WO | 2005087140 | 9/2005 |
| WO | 2006000763 | 1/2006 |
| WO | 2006000776 | 1/2006 |
| WO | 2006002492 | 1/2006 |
| WO | 2006004679 | 1/2006 |
| WO | 2006005015 | 1/2006 |
| WO | 2006009690 | 1/2006 |
| WO | 2006011127 | 2/2006 |
| WO | 2006012011 | 2/2006 |
| WO | 2006012013 | 2/2006 |
| WO | 2006012038 | 2/2006 |
| WO | 2006012068 | 2/2006 |
| WO | 2006012322 | 2/2006 |
| WO | 2006019498 | 2/2006 |
| WO | 2006026371 | 3/2006 |
| WO | 2006026377 | 3/2006 |
| WO | 2006026912 | 3/2006 |
| WO | 2006027499 | 3/2006 |
| WO | 2006028821 | 3/2006 |
| WO | 2006029062 | 3/2006 |
| WO | 2006031436 | 3/2006 |
| WO | 2006031469 | 3/2006 |
| WO | 2006032051 | 3/2006 |
| WO | 2006034245 | 3/2006 |
| WO | 2006035415 | 4/2006 |
| WO | 2006041505 | 4/2006 |
| WO | 2006044679 | 4/2006 |

(56) References Cited

FOREIGN PATENT DOCUMENTS

| | | |
|---|---|---|
| WO | 2006048664 | 5/2006 |
| WO | 2006050459 | 5/2006 |
| WO | 2006050460 | 5/2006 |
| WO | 2006054107 | 5/2006 |
| WO | 2006054930 | 5/2006 |
| WO | 2006055982 | 5/2006 |
| WO | 2006060546 | 6/2006 |
| WO | 2006064490 | 6/2006 |
| WO | 2006065212 | 6/2006 |
| WO | 2006065930 | 6/2006 |
| WO | 2006066148 | 6/2006 |
| WO | 2006066150 | 6/2006 |
| WO | 2006069094 | 6/2006 |
| WO | 2006070372 | 7/2006 |
| WO | 2006073628 | 7/2006 |
| WO | 2006076890 | 7/2006 |

OTHER PUBLICATIONS

International search report Nov. 13, 2006 6 pages.

* cited by examiner

VENOUS VALVE, SYSTEM, AND METHOD

CROSS-REFERENCE TO RELATED APPLICATIONS

This application is a continuation of U.S. application Ser. No. 11/150,331, filed Jun. 10, 2005, the contents of which is incorporated herein by reference.

FIELD OF THE INVENTION

The present invention relates to apparatus, systems, and methods for use in a lumen; and more particularly to a valve apparatus, systems, and methods for use in the vasculature system.

BACKGROUND OF THE INVENTION

The venous system of the legs uses valves and muscles as part of the body's pumping mechanism to return blood to the heart. Venous valves create one way flow to prevent blood from flowing away from the heart. When valves fail, blood can pool in the lower legs resulting in swelling and ulcers of the leg. The absence of functioning venous valves can lead to chronic venous insufficiency.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site. Prosthetic valves can be transplanted into the venous system, but current devices are not successful enough to see widespread usage.

DETAILED DESCRIPTION

Figure 1A:
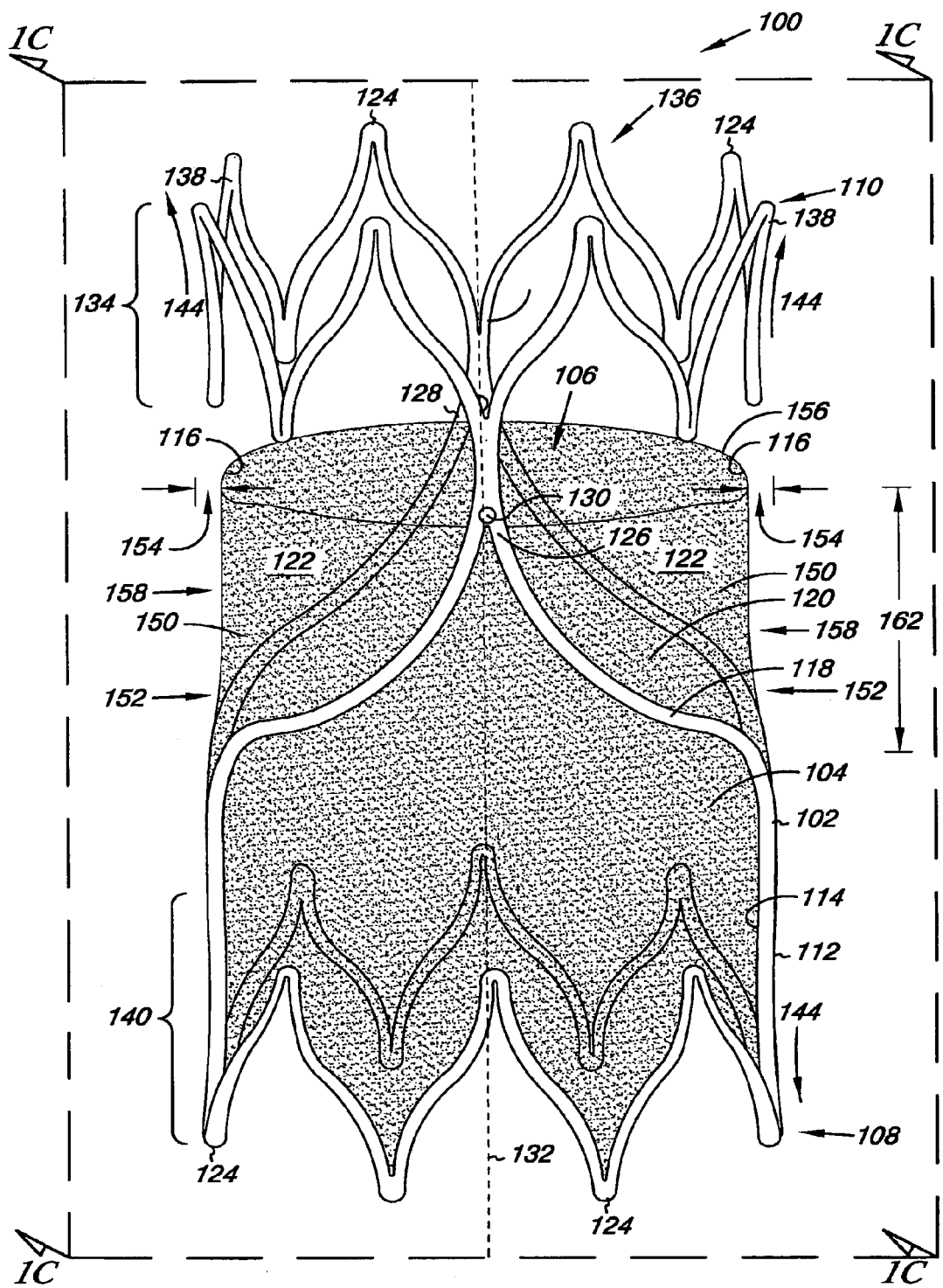
FIGS. 1A and 1B illustrate an embodiment of a valve according to the present invention.

Embodiments of the present invention are directed to an apparatus, system, and method for valve replacement or augmentation. For example, the apparatus can include a valve that can be used to replace or augment an incompetent valve in a body lumen. Embodiments of the valve can include a frame and cover that can be implanted through minimally-invasive techniques into the body lumen. In one example, embodiments of the apparatus, system, and method for valve replacement or augmentation may help to maintain antegrade blood flow, while decreasing retrograde blood flow in a venous system of individuals having venous insufficiency, such as venous insufficiency in the legs.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one Fig. can also apply to the element shown in one or more additional Figs. Embodiments illustrated in the figures are not necessarily to scale.

FIGS. 1A through 5B provide illustrations of various embodiments of a valve of the present invention. The valve can be implanted within the fluid passageway of a body lumen, such as for replacement or augmentation of a valve structure within the body lumen (e.g., a venous valve). In one embodiment, the valve of the present invention may be beneficial to regulate the flow of a bodily fluid through the body lumen in a single direction.

FIGS. 1A-1F illustrate one embodiment of a venous valve 100. Venous valve 100 includes a frame 102 and a cover 104 for the venous valve 100, where both the frame 102 and the cover 104 can resiliently radially collapse and expand, as will be described herein. Among other things, the frame 102 and the cover 104 define a lumen 106 of the valve 100. The lumen 106 allows for, amongst other things, fluid (e.g., blood) to move through the valve 100. The frame 102 also includes a first end 108 and a second end 110. The first end 108 and the second end 110 define a length of the frame 102 and of the valve 100. In one embodiment, the length of valve 100 can have a number of values. As will be appreciated, the length of valve 100 can be determined based upon the location into which the valve 100 is to be implanted. In other words, the length of the valve 100 can be patient specific. Examples of values for the length include, but are not limited to, 12 millimeters to 32 millimeters. Other values are also possible.

The frame 102 further includes an outer surface 112 and an inner surface 114 opposite the outer surface 112. In one embodiment, the cover 104 can be located over at least the outer surface 112 of the frame 102. For example, the cover 104 can extend around a perimeter of the frame 102 so as to completely cover the outer surface 112 of the frame 102. In other words, the cover 104 extends over the outer surface 112 of the frame 102 so that there are no exposed portions of the outer surface 112 of the frame 102. In an additional embodiment, the cover 104 can also be located over at least the inner surface 114 of the frame 102, as illustrated in FIGS. 1A-1F. A further embodiment includes the cover 104 located over at least a portion of the outer surface 112 and at least a portion of the inner surface 114.

The cover 104 can further include surfaces defining a reversibly sealable opening 116 for unidirectional flow of a liquid through the lumen 106. For example, the surfaces of the cover 104 can be deflectable between a closed configuration in which fluid flow through the lumen 106 can be restricted and an open configuration in which fluid flow through the lumen 106 can be permitted.

The frame 102 can be formed from a wide variety of materials and in a wide variety of configurations. Frame 102 can have a unitary structure with an open frame configuration. For example, the open frame configuration can include frame members 118 that define openings 120 across the frame 102 through which valve leaflets 122 formed by the cover 104 can radially-collapse and radially-expand, as will be described herein.

In addition, the first end 108 and the second end 110 each include a plurality of end portions 124 that lay on a common plane. The plurality of end portions 124, however, need not all lay on the common plane. In other words, it is possible that one or more of the end portions 124 of the frame 102 lay above and/or below the common plane.

While the frames illustrated herein, for example frame 102, are shown as having a circular configuration, other configurations are also possible. For example, the frame 102 could have an elliptical configuration. As such, the present invention should not be limited to the illustration of the frames, such as frame 102, provided herein.

As illustrated in FIGS. 1A-1F, the frame 102 can further include a first leaflet connection region 126 and a second leaflet connection region 128 adjacent the second end 110 of the frame 102. The first and second leaflet connection regions 126 and 128 further include an opening 130 through the frame 102. In the present example, the cover 104 can be coupled, as described more fully herein, to at least the first leaflet connection region 126 and the second leaflet connection region 128 using the openings 130 through the frame 102. The cover 104 so coupled can then move (e.g., pivot) relative the first leaflet connection region 126 and the second leaflet connection region 128 between an open valve configuration (illustrated in FIGS. 1A, 1C, and 1E) and a closed valve configuration (illustrated in FIGS. 1B, 1D, and 1F). As illustrated in the closed valve configuration, the open frame configuration of frame 102 allows cover 104 to move through the openings 120 in creating the reversible sealable opening 116 of the valve 100.

As illustrated in FIGS. 1A-1B and 1E-1F, the first leaflet connection region 126 and the second leaflet connection region 128 can be positioned opposite each other along a common axis. In addition, the first leaflet connection region 126 and the second leaflet connection region 128 can be radially symmetric around the longitudinal central axis 132 of the frame 102.

As illustrated, the first leaflet connection region 126 and the second leaflet connection region 128 can be positioned approximately one hundred eighty (180) degrees relative each other around the longitudinal central axis 132 of the frame 102. As will be appreciated, the first and second leaflet connection regions 126, 128 need not necessarily display an equally spaced symmetrical relationship as described above in order to practice the embodiments of the present invention. For example, the radial relationship can have the first and second leaflet connection region 126, 128 positioned at values greater than one hundred eighty (180) degrees and less than one hundred eighty (180) degrees relative each other around the longitudinal central axis 132 of the frame 102.

The frame member 118 of frame 102 can have similar and/or different cross-sectional geometries and/or cross-sectional dimensions along its length. The similarity and/or the differences in the cross-sectional geometries and/or cross-sectional dimensions can be based on one or more desired functions to be elicited from each portion of the frame 102. For example, the frame member 118 can have a similar cross-sectional geometry along its length. Examples of cross-sectional geometries include, but are not limited to, round (e.g., circular, oval, and/or elliptical), rectangular geometries having perpendicular sides, one or more convex sides, or one or more concave sides; semi-circular; triangular; tubular; I-shaped; T shaped; and trapezoidal.

Alternatively, the cross-sectional dimensions of one or more geometries of the frame member 118 can change from one portion of the frame 102 to another portion of the frame 102. For example, portions of the frame member 118 can taper (i.e., transition) from a first geometric dimension to a second geometric dimension different than the first geometric dimension. These embodiments, however, are not limited to the present examples as other cross-sectional geometries and dimension are also possible. As such, the present invention should not be limited to the frames provided in the illustration herein.

The valve 100 can further include a radial support member 134. The radial support member 134 can include a number of different configurations, as will be described herein. For example, as illustrated the radial support member 134 couples the first leaflet connection region 126 and the second leaflet connection region 128. In addition to coupling the connection regions 126 and 128, the radial support member 134 can also serve to stabilize the relative positions of the connection regions 126 and 128 (e.g., limit relative fluctuations of the connection regions 126 and 128).

In the present embodiment, the radial support member 134 can be in the form of a tubular ring 136. The tubular ring 136 joins to the first leaflet connection region 126 and the second leaflet connection region 128. The tubular ring 136 can also move radially with the first and second leaflet connection region 124, 126 as the valve 100 radially collapses and expands.

In the various embodiments described herein, the tubular ring 136 can be configured to provide a spring force (e.g., elastic potential energy) to counter radial compression of the frame 102 towards its uncompressed state. For example, the tubular ring 136 can have a zig-zag configuration that includes corners 138 in from which a spring force (e.g., elastic potential energy) can be derived when the frame 102 is compressed. As will be appreciated, the corners 138 can have a number of configurations, including turns defining angles and/or arcs (e.g., having a radius of curvature). Additional spring force can be imparted to the frame 102 from the compression of the corners adjacent the first and second leaflet connection regions 126, 128 as well.

The valve 100 can further include a second tubular ring 140 located at the first end 108 of the frame 102. The second tubular ring 140 can have a similar, or different, configuration as tubular ring 136 so as to impart the spring force to counter radial compression of the frame 102 towards its uncompressed state. In one embodiment, both the tubular ring 136 and the second tubular ring 140 help to stabilize the relative positions of the connection regions 126 and 128, as described herein, and to help maintain the position of the connection regions 126 and 128 relative the walls of a lumen in which the valve 100 has been implanted. As will be appreciated, the valve 100 could further include additional tubular rings located at one or more positions along the frame 102.

The compressible nature of the valve 100 can accommodate changes in body lumen size (e.g., diameter of the body lumen) by flexing to expand and/or contract to change the diameter of the frame 102. In one embodiment, the corner portions of the tubular rings 136 and 140, and the first leaflet connection region 126 and the second leaflet connection region 128 can act as springs to allow the valve 100 to resiliently radially collapse and expand. The frame 102 can also provide sufficient contact and expansion force with the surface of a body lumen wall to encourage fixation of the valve 100 and to prevent retrograde flow within the body lumen around the edges of the frame 102 and the surface of a lumen when combined with a closed state of the valve leaflets attached thereto. Anchoring elements (e.g., barbs) can also be included with valve 100.

Figure 2B:
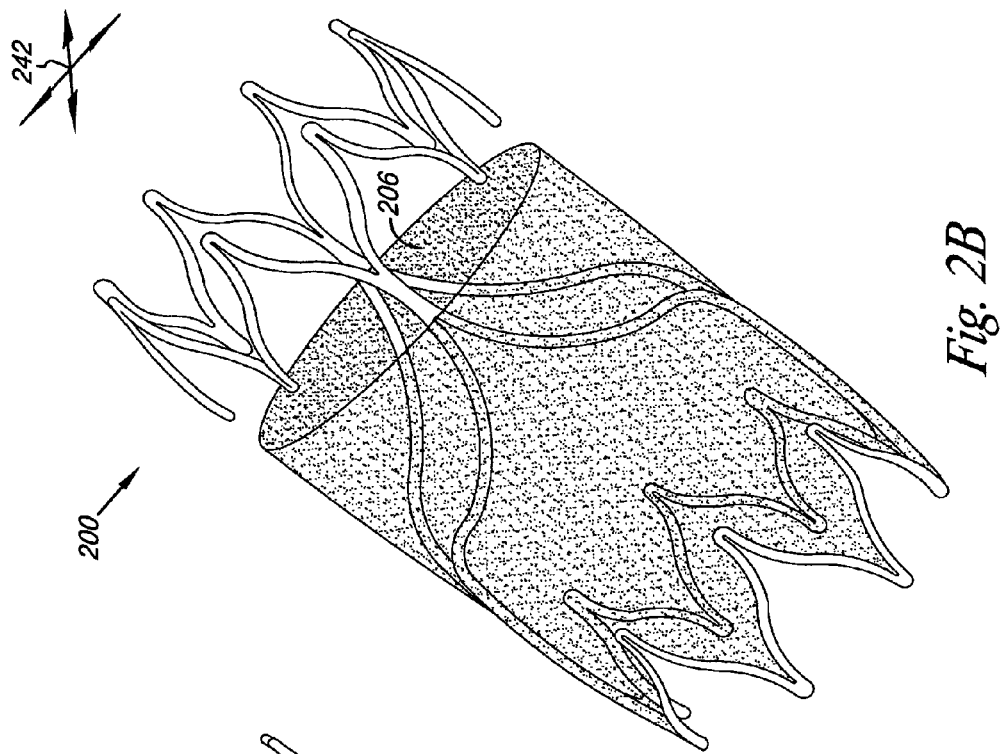
FIGS. 2A and 2B illustrate an embodiment of a valve in an expanded and collapsed state according to the present invention.
Figure 2A:
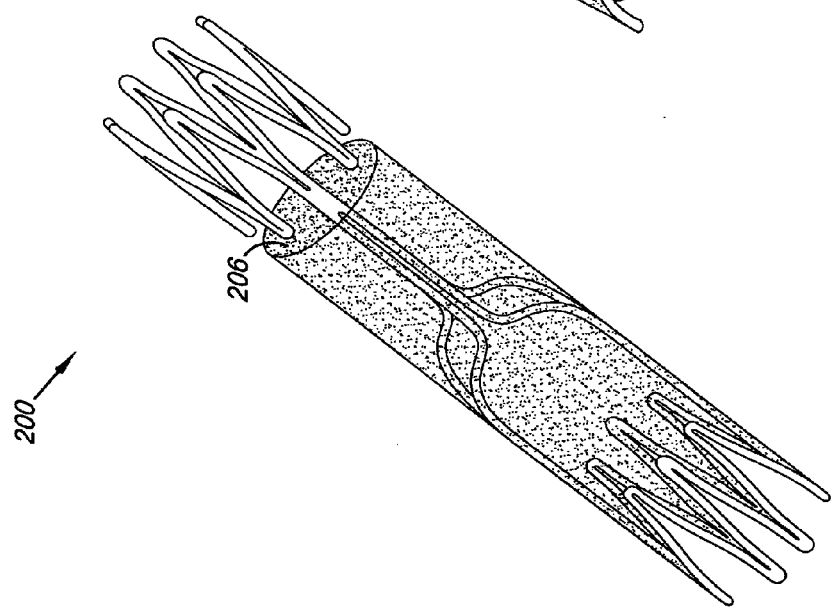

FIGS. 2A and 23 provide an example of the valve 200 in a collapsed state (FIG. 2A) and in an expanded state (FIG. 2B). As shown in FIGS. 2A and 2B, the valve 200 can travel between the collapsed and the expanded state along a radial travel path 240 (as shown in FIG. 2B), where there can be a change in a cross sectional area of lumen 206. For example, the frame 202 can travel along the radial travel path 242 so as to change a width of lumen 206. This can allow the valve 200 to react appropriately to the distension and contraction of a body lumen in which the valve 200 is placed.

Referring again to FIGS. 1A-1F, the corner portions of the tubular rings 136 and 140, and the first and second leaflet connection region 126 and 128 can also include, but are not limited to, other shapes that allow for repeatable travel between the collapsed state and the expanded state. For example, the elastic regions can include integrated springs having a circular or an elliptical loop configuration. The embodiments are not, however, limited to these configurations as other shapes are also possible.

The frame member 118 forming the tubular rings 136 and 140 can also include a radial flare 144. As illustrated, the radial flare 144 provides for an increase in the peripheral frame dimension at the first end 108 and/or the second end 110 of the frame 102. In one embodiment, the frame members 118 can be pre and/or post-treated to impart the radial flare 144. For example, frame members 118 forming the tubular rings 136 and 140 of the frame 102 could be bent to impart the radial flare 144. The frame 102 could then be heat treated so as to fix the radial flare 144 into the frame member 118. Other material treatments (e.g., plastic deformation, forging, elastic deformation with heat setting) are also possible to impart the radial flare as described herein, many of which are material specific.

The embodiments of the frame described herein can also be constructed of one or more of a number of materials and in a variety of configurations. The frame embodiments can have a unitary structure with an open frame configuration. The frame can also be self-expanding. Examples of self-expanding frames include those formed from temperature-sensitive memory alloy which changes shape at a designated temperature or temperature range, such as Nitinol. Alternatively, the self-expanding frames can include those having a spring-bias. In addition, the frame 102 can have a configuration that allows the frame embodiments be radially expandable through the use of a balloon catheter.

The embodiments of the frame, such as frame 102 in FIGS. 1A-1F, can also be formed from one or more contiguous frame members. For example, the frame member 118 of frame embodiments can be a single contiguous member. The single contiguous member can be bent around an elongate tubular mandrel to form the frame. The free ends of the single contiguous member can then be welded, fused, crimped, or otherwise joined together to form the frame. In an additional embodiment, the frame member 118 of frame 102 can be derived (e.g., laser cut, water cut) from a single tubular segment. In an alternative embodiment, methods of joining the frame member 118 to create the elastic region include, but are not limited to, welding, gluing, and fusing the frame member. The frame 102 can be heat set by a method as is typically known for the material which forms the frame 102.

The frame embodiments can be formed from a number of materials. For example, the frame can be formed from a biocompatible metal, metal alloy, polymeric material, or combination thereof. As described herein, the frame can be self-expanding or balloon expandable. In addition, the frame can be configured so as to have the ability to move radially between the collapsed state and the expanded state. Examples of suitable materials include, but are not limited to, medical grade stainless steel (e.g., 316L), titanium, tantalum, platinum alloys, niobium alloys, cobalt alloys, alginate, or combinations thereof. Additional frame embodiments may be formed from a shape-memory material, such as shape memory plastics, polymers, and thermoplastic materials. Shaped memory alloys having superelastic properties generally made from ratios of nickel and titanium, commonly known as Nitinol, are also possible materials. Other materials are also possible.

The lumen 106 can include a number of sizes. For example, the size of the lumen can be determined based upon the type of body lumen and the body lumen size in which the valve is to be placed. In an additional example, there can also be a minimum value for the width for the frame that ensures that the frame will have an appropriate expansion force against the inner wall of the body lumen in which the valve is being placed.

In one embodiment, the frame can further include one or more active anchoring elements. For example, the one or more active anchoring elements can include, but are not limited to, one or more barbs projecting from the frame 102.

The valve can further include one or more radiopaque markers (e.g., tabs, sleeves, welds). For example, one or more portions of the frame can be formed from a radiopaque material. Radiopaque markers can be attached to, electroplated, dipped and/or coated onto one or more locations along the frame. Examples of radiopaque material include, but are not limited to, gold, tantalum, and platinum.

The position of the one or more radiopaque markers can be selected so as to provide information on the position, location and orientation (e.g., axial, directional, and/or clocking position) of the valve during its implantation. For example, radiopaque markers can be configured radially (e.g., around the radial support members 132 and 134) and longitudinally (e.g., on predetermined portions of longitudinally extending frame members 118) on predetermined portions of the frame 102 to allow the radial and axial position of the frame 102 to be determined. So in one embodiment a radiograph image of the frame 102 taken perpendicular to the valve leaflets 122 in a first clock position can produce a first predetermined radiograph image (e.g., an imaging having the appearance of an inverted "Y") and a radiographic image taken perpendicular to the first and second leaflet connection regions 126, 128 in a second clock position can produce a second predetermined radiograph image (e.g., an imaging having the appearance of an upright "Y") distinguishable from the first predetermined radiograph image.

In one embodiment, the first and second predetermined radiograph images allow the radial position of the leaflets 122 to be better identified within the vessel. This then allows a clocking position for the valve 100 to be determined so that the valve can be positioned in a more natural orientation relative the compressive forces the valve will experience in situ. In other words, determining the clocking of the valve as described herein allows the valve to be radially positioned in same orientation as native valve that it's replacing and/or augmenting.

As described herein, valve 100 further includes cover 104 having surfaces defining the reversibly sealable opening 116 for unidirectional flow of a liquid through the lumen 106. In one embodiment, the cover 104 extends over at least a portion of the frame 102 to the first and second leaflet connection regions 126, 128. The cover 104 extends between the first and second leaflet connection regions 126, 128 to provide a first valve leaflet 146 and a second valve leaflet 148 of the valve leaflets 122. The first and second valve leaflets 146, 148 include surfaces defining the reversibly sealable opening 116 extending between the first and second leaflet connection regions 126, 128 for unidirectional flow of a liquid through the valve 100.

In one embodiment, the material of the cover 104 can be sufficiently thin and pliable so as to permit radially-collapsing of the valve leaflets 122 for delivery by catheter to a location within a body lumen. The valve leaflets 122 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethlylene (PE), polyethylene terephthalate (PET), silk, Rayon, Silicone, or the like. Possible biologic materials include, but are not limited to, autologous, allogeneic or xenograft material. These include explanted veins and decellularized basement membrane materials (such as noncrosslinked bladder membrane or amnionic membrane), such as small intestine submucosa (SIS) or umbilical vein. As will be appreciated, blends or mixtures of two or more of the materials provided herein are possible. For example, SIBS can be blended with one or more basement membrane materials.

As described herein, a number of methods exist for attaching the cover 104 to the frame 102 so as to form the valve leaflets 122. For example, when positioned over the inter surface 114 of the frame 102, the cover 104 can be secured to the frame members 118 through the use of biocompatible staples, glues, sutures or combinations thereof. In an additional embodiment, the cover 104 can be coupled to the frame members 118 through the use of heat sealing, solvent bonding, adhesive bonding, or welding the cover 104 to either a portion of the cover 104 (i.e., itself) and/or the frame 102.

With respect to coupling the cover 104 to the first and second leaflet connection regions 126, 128, the cover 104 can be passed from the inner surface 114 and wrapped around at least a portion of the outer surface 112 adjacent the connection regions. For example, securing the cover 104 at the first and second leaflet connection regions 126, 128 can be accomplished by making longitudinal cuts of a predetermined length into the cover 104 adjacent the first and second leaflet connection regions 126, 128. In one embodiment, each cut creates two flaps adjacent each of the first and second leaflet connection regions 126, 128. The flaps can then pass through the frame adjacent the first and second leaflet connection regions 126, 128 and each of the two resulting flaps can be wrapped from the inner surface 114 around the frame 102 to the outer surface 112. The cover 104 can then be coupled to itself and/or the frame 102, as described herein. In addition, sutures can be passed through the opening 130 and the cover 104 so as to secure the cover 104 to the frame 102. In one embodiment, providing the flaps as described allows for the cover 104 to create a more fluid tight opening 116 in the area adjacent the first and second connection regions 126, 128.

As illustrated, the valve leaflets 122 include a region 150 of the cover 104 that can move relative the frame 102. The region 150 of the cover 104 can be unbound (i.e., unsupported) by the frame 102 and extends between the first and second leaflet connection regions 126, 128. This configuration permits the reversibly sealable opening 116 to open and close in response to the fluid pressure differential across the valve leaflets 122.

In an additional embodiment, the valve leaflets 122 in their open configuration have a circumference that is less than the circumference of the frame 102. For example, as illustrated, the valve leaflets 122 in their open configuration (FIG. 1A) include a transition region 152 where the circumference of the cover 104 changes from a first circumference to a second circumference that is smaller than the first circumference. In one embodiment, this better ensures that the valve leaflets 122 do not come into contact with the inner wall of the vessel in which the valve 100 is implanted.

In addition, the transition region 152 allows for a gap 154 between the outer surface of the valve leaflets 122 and the inner wall of the vessel in which the valve 100 is implanted. In one embodiment, the gap 154 can help prevent adhesion between the valve leaflets 122 and the vessel wall due to the presence of a volume of blood there between. The gap 154 can also allow for retrograde blood flow to be collected as the process of closing the valve leaflets 122 starts.

Figure 1B:
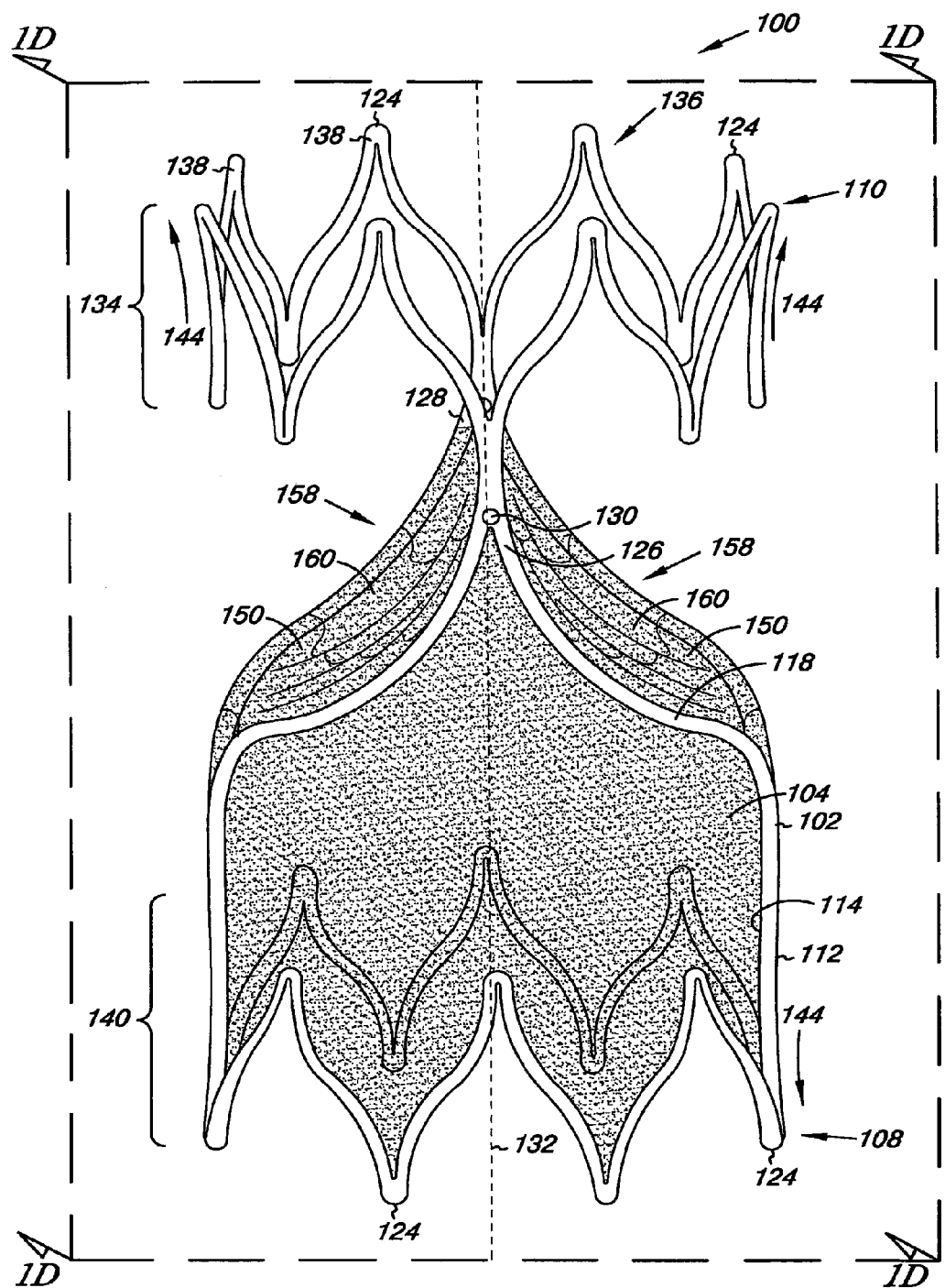
Figure 1C:
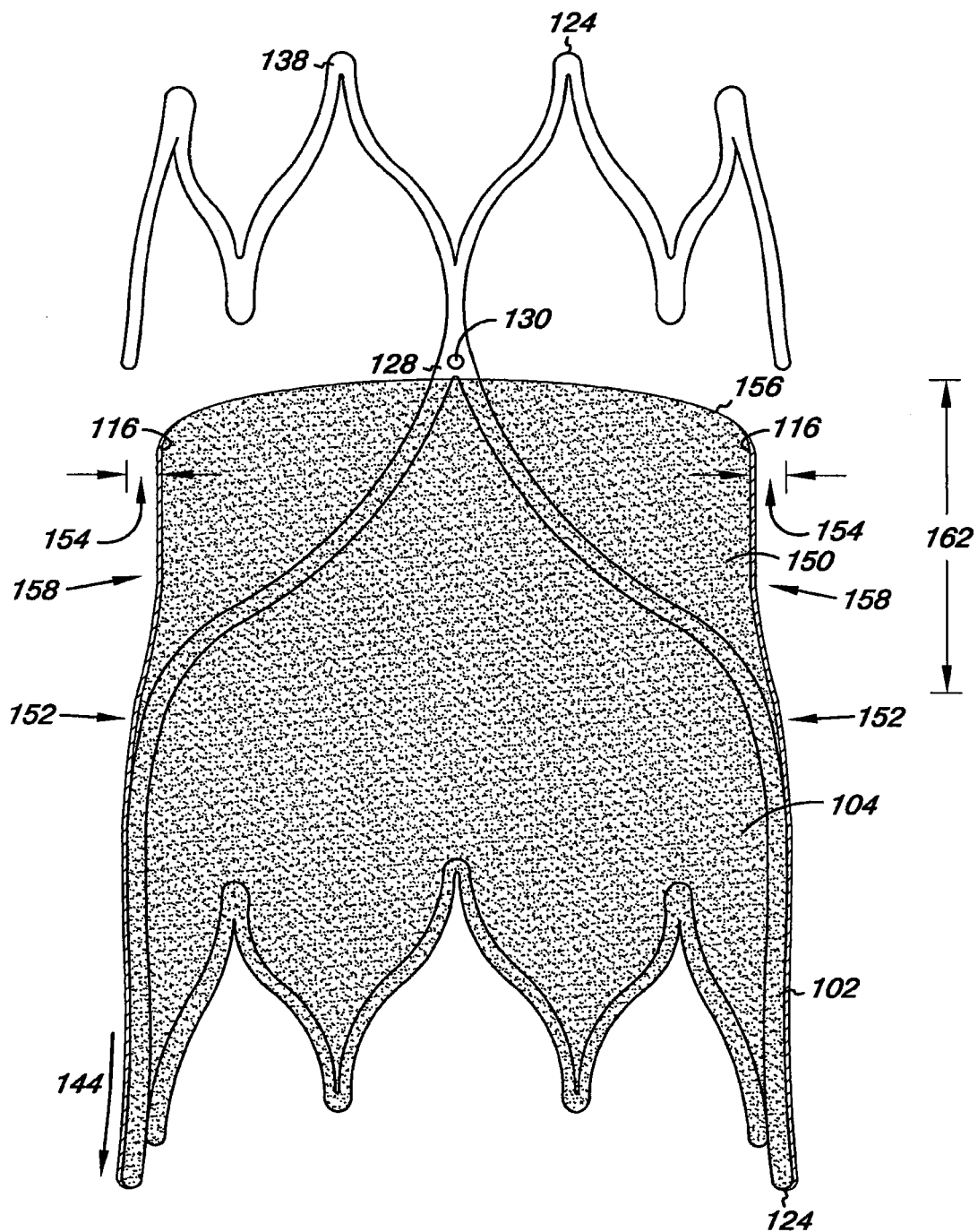
FIG. 1C illustrates a cross-sectional view of the valve illustrated in FIG. 1A.
Figure 1D:
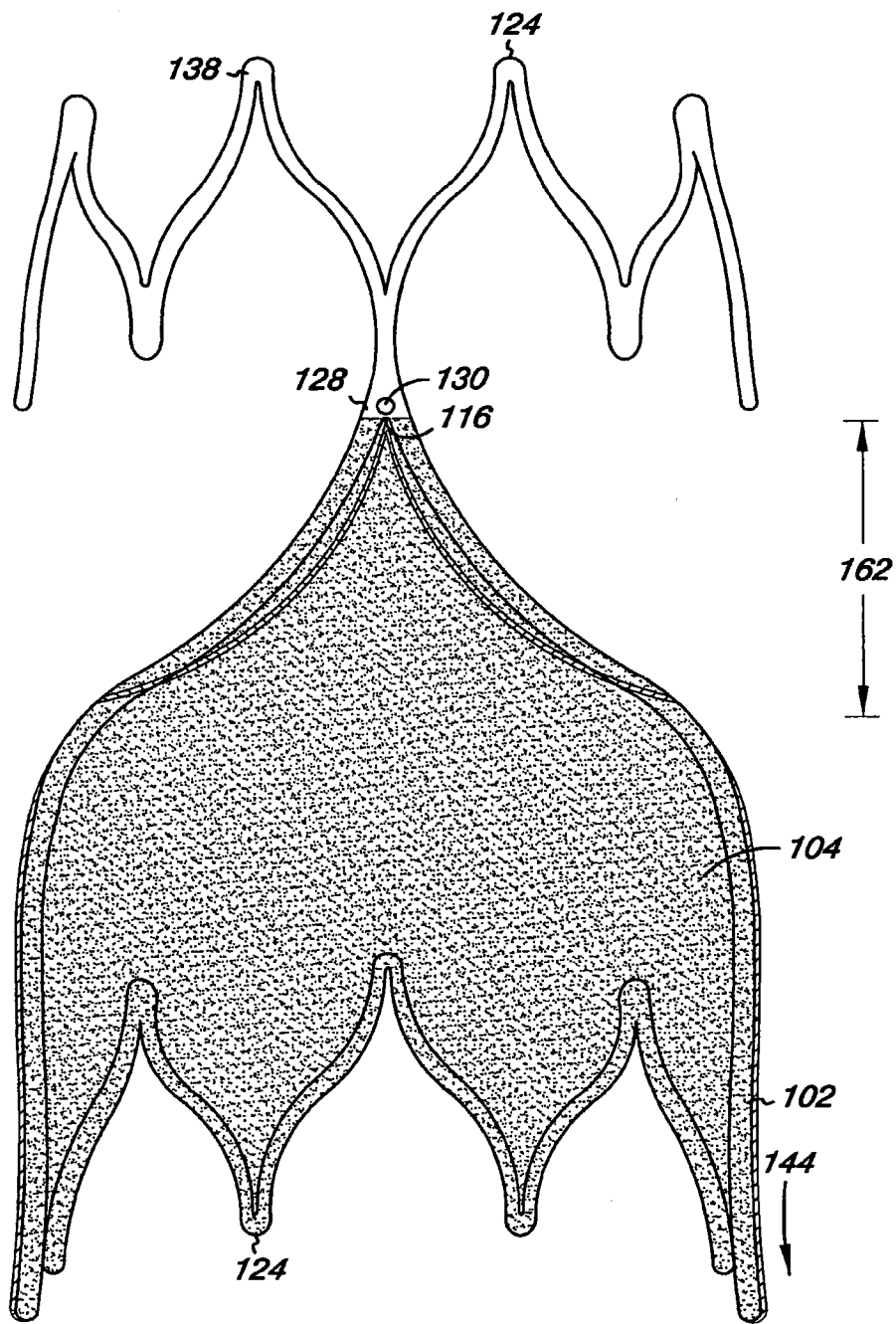
FIG. 1D illustrates a cross-sectional view of the valve illustrated in FIG. 1B.
Figure 1E:
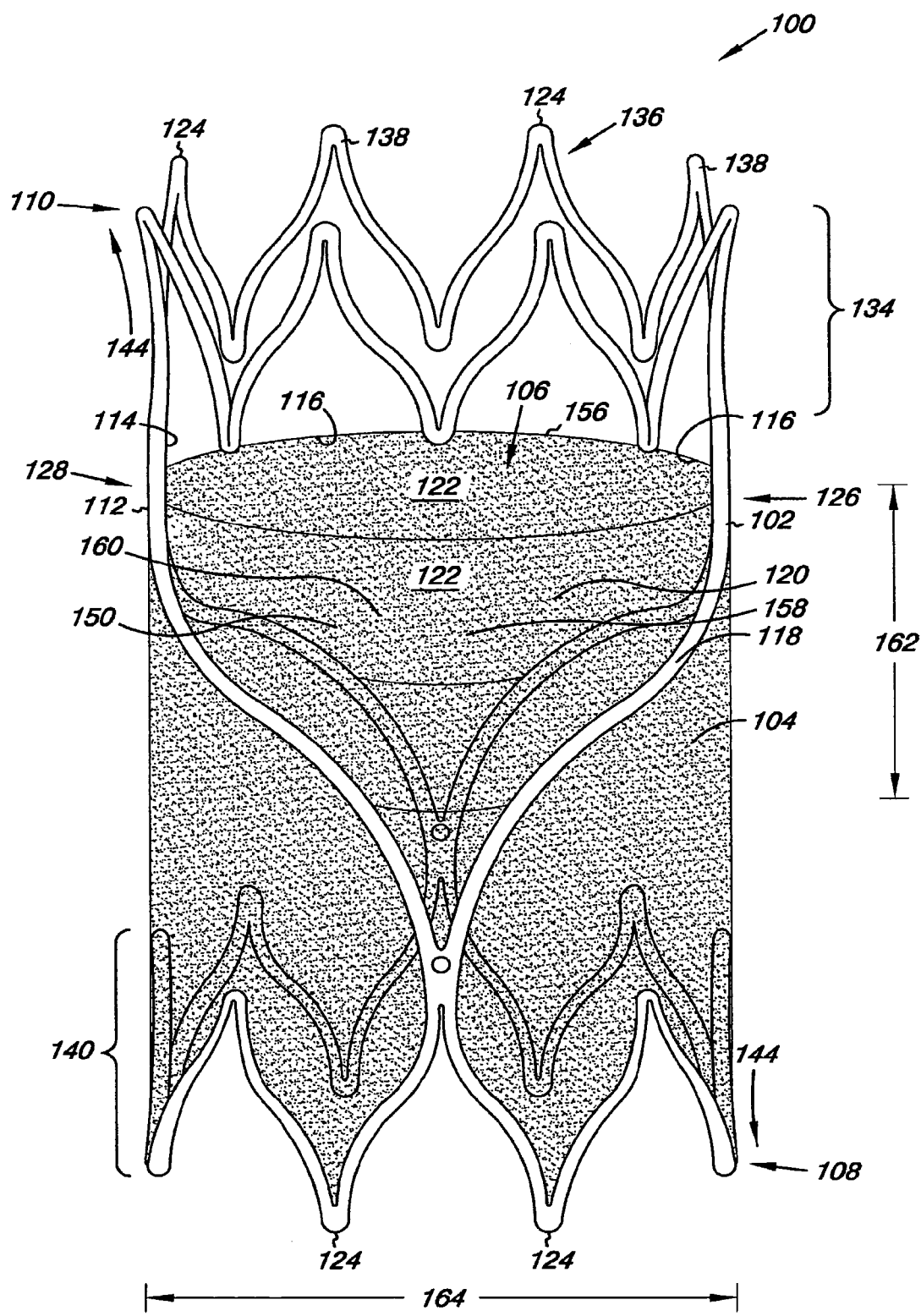
FIGS. 1E and 1F illustrates an additional perspective view of the valve illustrated in FIG. 1A.
Figure 1F:
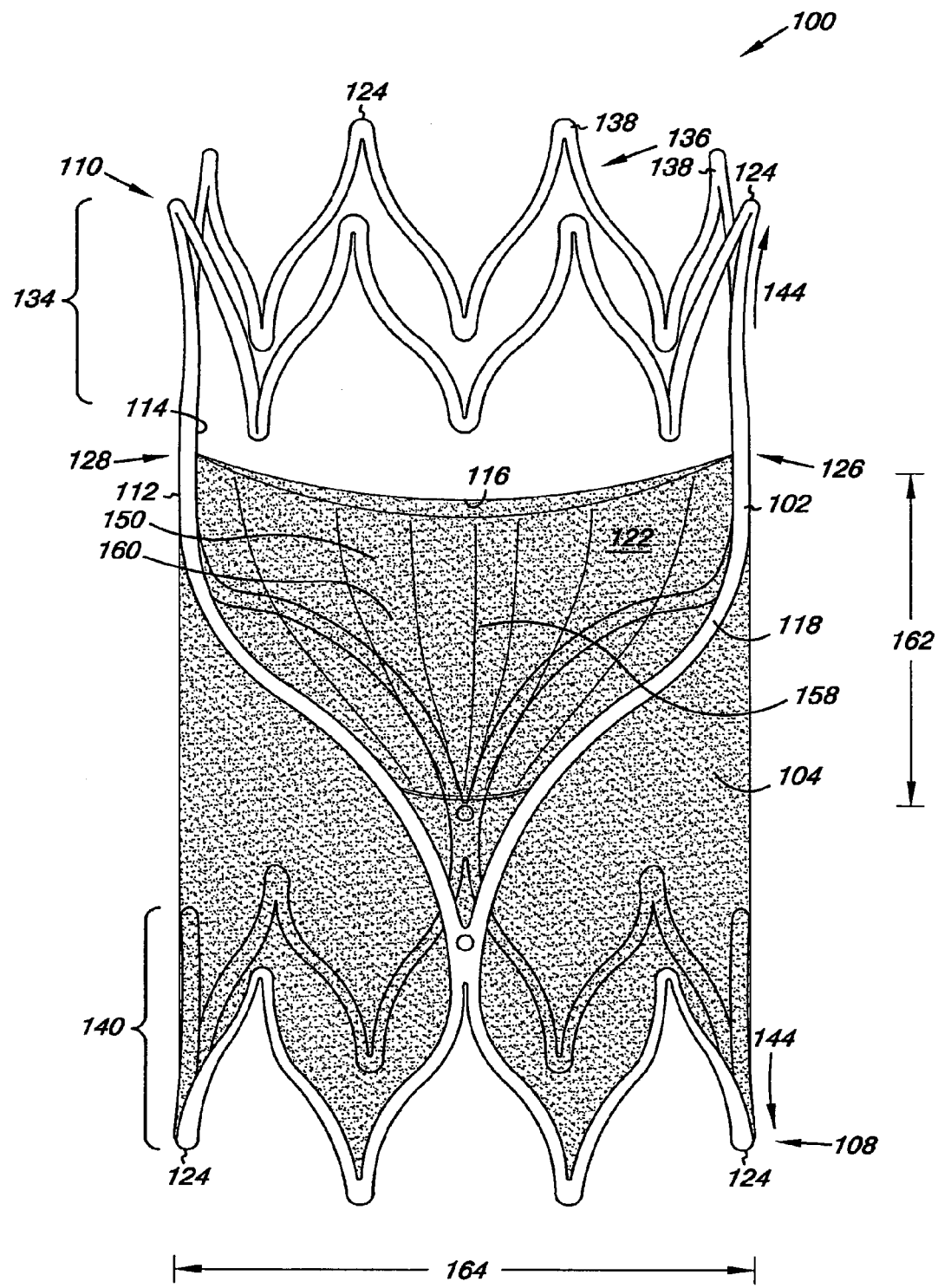

In one embodiment, the reversible scalable opening 116 also includes a lip 156. The lip 156 can have either a non-planar or a planar configuration. In one embodiment, whether the lip 156 has a planar or non-planar configuration can depend on what material is selected for forming the valve leaflets 122. For example, when a stiffer material (e.g., PTFE) is used for the valve leaflets 122 the lip 156 can have more of a concave shape than a planar or straight shape. In other words, as illustrated in FIGS. 1A and 1E, the lip 156 transitions from a first position adjacent the first and second leaflet connection regions 126, 128 to a second position lower than the first position as illustrated approximately midway between the first and second leaflet connection regions 126, 128. So, the lip 156 dips down to a low point approximately midway between the first and second leaflet connection regions 126, 128. In one embodiment, this shape allows the lip 156 to form a catenary when the valve leaflets 122 are in their closed position, as illustrated in FIG. 1F. In an alternative embodiment, when an elastic material is used for the valve leaflets 122 the lip 156 has more of a straight or planar shape. In other words, the lip 156 maintains essentially the same relative position around the circumference of the valve leaflets 122.

As will be appreciated, the lip 156 when the valve leaflets 122 are in their open configuration can have a non-round shape. For example, the lip 156 can have an eye shape or an oval shape with the major axis extending between the first and second leaflet connection regions 126, 128.

In one embodiment, under antegrade fluid flow (i.e., positive fluid pressure) from the first end 108 towards the second end 110 of the valve 100, the valve leaflets 122 can expand toward the inner surface 114 of the frame 102 to create an opening through which fluid is permitted to move. In one example, the valve leaflets 122 each expand to define a semi-tubular structure having an oval cross-section when fluid opens the reversibly sealable opening 116. An example of the open configuration for the valve is shown in FIGS. 1A, 1C and 1E.

Under a retrograde fluid flow (i.e., negative fluid pressure) from the second end 110 towards the first end 108, the valve leaflets 122 can move away from the inner surface 114 as the valve leaflets 122 begin to close. In one example, the gap 154 allows fluid from the retrograde flow to develop pressure on a first major face 158 of the valve leaflets 122. As fluid pressure develops, the valve leaflets 122 collapse, closing the reversibly sealable opening 116, thereby restricting retrograde fluid flow through the valve 100. An example of the closed configuration for the valve is shown in FIGS. 1B, 1D, and 1F.

In an additional embodiment, the first major surface 158 of the valve leaflet 121 further include a concave pocket 160. For example, as illustrated in FIGS. 1E and 1F, the concave pocket 160 can be defined by a predefined portion of the cover 104 that moves relative the frame 102 as the valve opens and closes. In one embodiment, the concave pocket 160 includes specific dimensions relative a diameter of a vessel into which the valve 100 is to be implanted. For example, the concave pocket 160 can have a predetermined length-to-width ratio relative the diameter of the vessel in which the valve 100 is to be implanted. In one embodiment, the predetermined length-to-width ratio can be defined as:

$$H=(0.75)(D)$$

where H is the maximum height 162 of concave pocket 160, and D is a diameter 164 of the valve 100 taken between the first and second leaflet connection regions 126, 128.

Valve 100 provides an embodiment in which the surfaces defining the reversibly sealable opening 116 provide a bi-leaflet configuration (i.e., a bicuspid valve) for valve 100. Although the embodiments in FIGS. 1A-1F illustrate and describe a bi-leaflet configuration for the valve of the present invention, designs employing a different number of valve leaflets (e.g., tri-leaflet valve) may be possible. For example, additional connection points (e.g., three or more) could be used to provide additional valve leaflets (e.g., a tri-leaflet valve).

The valve leaflets 122 can have a variety of sizes and shapes. For example, each of the valve leaflets 122 can have a similar size and shape. Alternatively, each of the valve leaflets 122 need not have a similar size and shape (i.e., the valve leaflets can have a different size and shape with respect to each other).

In an additional embodiment, the valve leaflets 122 can include one or more support structures, where the support structures can be integrated into and/or onto the valve leaflets 122. For example, the valve leaflets 122 can include one or more support ribs having a predetermined shape. In one embodiment, the predetermined shape of the support ribs can include a curved bias so as to provide the valve leaflets 122 with a curved configuration. Support ribs can be constructed of a flexible material and have dimensions (e.g., thickness, width and length) and cross-sectional shape that allows the support ribs to be flexible when the valve leaflets 122 are urged into an open position, and stiff when the valve leaflets 122 are urged into a closed position upon experiencing sufficient back flow pressure from the direction downstream from the valve. In an additional embodiment, support ribs can also be attached to frame 102 so as to impart a spring bias to the valve leaflets in either the open or the closed configuration.

As described herein, the cover 104 can be located over at least the inner surface 114 of the frame 102. FIGS. 1A and 1B illustrate an embodiment of this configuration, where the cover extending over the inner surface 114 also forms the valve leaflets 122 as described herein. Numerous techniques may be employed to laminate or bond cover 104 on the outer surface 112 and/or the inner surface 1114 of the frame 102, including heat setting, adhesive welding, application of uniform force and other bonding techniques. Additionally, the cover 104 may be folded over the first end 108 of the frame 102 to provide the cover 104 on both the outer surface 112 and the inner surface 114. Cover 104 can also be joined to itself and/or the members 118 according to the methods described in U.S. Patent Application Publication US 2002/0178570 to Sogard et al., which is hereby incorporated by reference in its entirety.

The cover 104 can also be coupled to the connection regions so as to form the valve leaflets, as described herein. In one embodiment, the cover 104 can be in the form of a sheet or a sleeve of material, as described herein, which can be connected to the frame 102. Alternatively, the cover 104 can initially be in the form of a liquid that can be used to cast and/or form the cover over the frame 102. Other forms, including intermediate forms, of the cover 104 are also possible.

The cover 104 can be coupled to the frame 102, including the connection regions 126 and 128, in a variety of ways so as to provide the various embodiments of the valve of the present invention. For example, a variety of fasteners can be used to couple the cover 104 to the frame 102 so as to form the valve 100. Suitable fasteners can include, but are not limited to, biocompatible staples, glues, sutures or combinations thereof. In an additional embodiment, the cover 104 can be coupled to the frame 102 through the use of heat sealing, solvent bonding, adhesive bonding, or welding cover 104 to either a portion of the cover 104 (i.e., itself) and/or the frame 102.

The cover 104, including the valve leaflets 122, may also be treated and/or coated with any number of surface or material treatments. For example, the cover 104 can be treated with one or more biologically active compounds and/or materials that may promote and/or inhibit endothelization and/or smooth muscle cell growth of the cover 104, including the valve leaflets 122. Similarly, the cover 104 may be seeded and covered with cultured tissue cells (e.g., endothelial cells) derived from a either a donor or the host patient which are attached to the valve leaflets 122. The cultured tissue cells may be initially positioned to extend either partially or fully over the valve leaflets 122.

Cover 104, in addition to forming valve leaflets 122, can also be capable of inhibiting thrombus formation. Additionally, cover 104 may either prevent or facilitate tissue ingrowth there through, as the particular application for the valve 100 may dictate. For example, cover 104 on the outer surface 112 may be formed from a porous material to facilitate tissue ingrowth there through, while cover 104 on the inner surface 114 may be formed from a material or a treated material which inhibits tissue ingrowth.

Figure 3A:
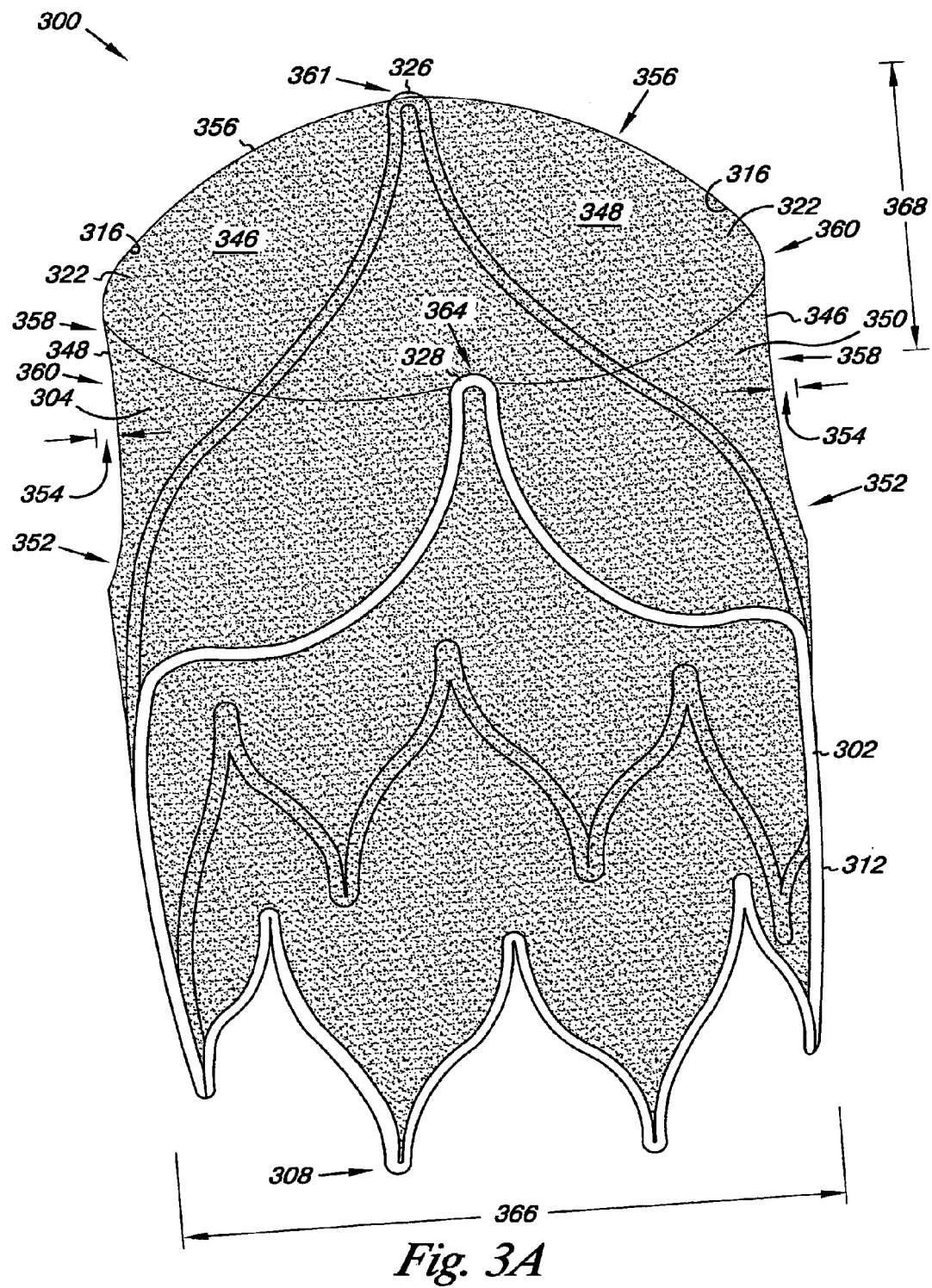
FIGS. 3A and 3B illustrate an embodiment of a valve according to the present invention.
Figure 3B:
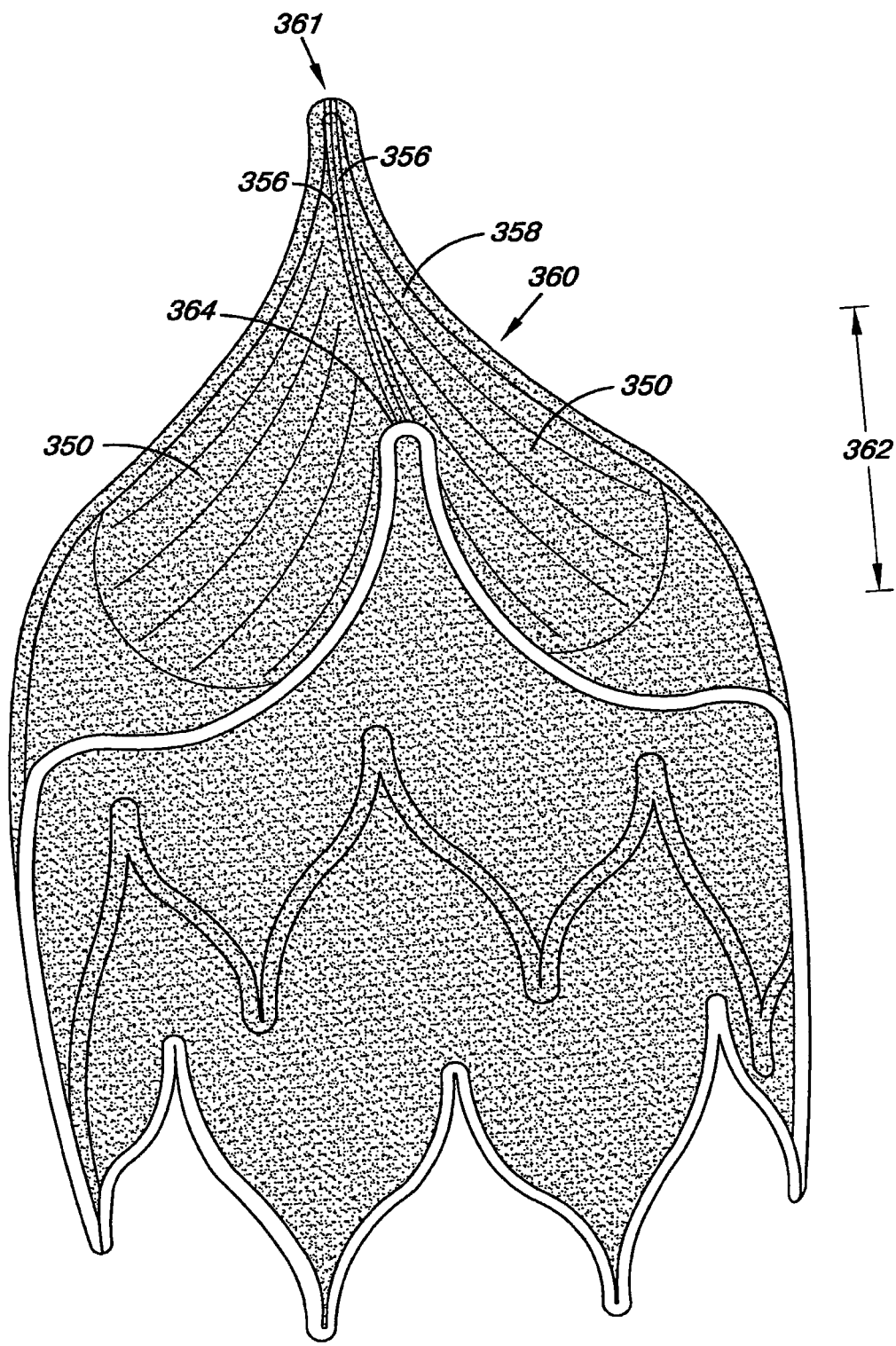

FIGS. 3A and 3B illustrate an additional embodiment of the valve 300. Valve 300 includes frame 302 having an open frame configuration and the first and second leaflet connection regions 326, 328, as described herein. The leaflet connection regions 326 and 328 also provide a first vertex 361 and a second vertex 364, respectively, relative the first end 308 of the frame 302.

As illustrated, the outer surface 312 of the frame 302 can provide a number of frame dimensions. For example, the outer surface 312 of the frame 302 can be viewed as defining a first frame dimension 366 at the first end 308 of the frame 302 and a second frame dimension 368 between the first vertex 361 and the second vertex 364 of the frame 302. In one embodiment, the second frame dimension 368 can have a larger value as compared to the first frame dimension 366. Other dimensional relationships between the first and second frame dimensions 366 and 368 are also possible.

In the present embodiment, the differences in the frame dimensions for frame 302 allow portions of the frame members 318 to provide the radial support member for the valve 300. In other words, the radial support member of the frame 302 can result from the relative shape and size of the different portions of the frame members 318. For example, as described herein the first and second frame dimensions 366, 368 can have different sizes, where the outer surface 312 of the frame 302 radially arcs from the first frame dimension 366 to the second frame dimension 368 so as to provide the radial support member of the frame 302.

So, in the present example the flaring of the of the frame member 318 from the first frame dimension 366 to the second frame dimension 368 allows the frame member 318 in the region of the first and second vertex 361 and 364 to provide the radial support member. In one embodiment, the frame members 318 can be pre and/or post treated to impart the frame dimension differences described herein. For example, frame members 318 forming the first vertex 361 and the second vertex 364 of the frame 302 could be bent to impart the radial flare. In one embodiment, a mandrel having a tapering surface could be used to impart the radial flare to the frame member 318.

The flared first and second vertex 361, 364 of the frame 302 could then be heat treated so as to fix the radial flare into the frame member 318. For example, a suitable heat treatment for a nitinol material can include heating the frame member 318 to approximately 500 degrees Celsius for approximately two (2) minutes. The frame members 318 can then be air cooled or quenched. Other material treatments (plastic deformation, forging, elastic deformation—heat setting) are also possible to impart the radial flare as described herein, many of which are material specific.

In one embodiment, the radial support member illustrated in FIG. 3 can serve to stabilize the valve 300 once positioned at a predetermined location as described herein. In addition, the configuration of the radial support member can allow the first frame dimension 366 and the second frame dimension 368 to more closely correspond to each other once the valve 300 has been positioned at the predetermined location.

The valve 300 can thither include the cover 304, where both the frame 302 and the cover 304 can resiliently radially collapse and expand, as described herein. In the present example, the cover 304 can be located over at least the outer surface 312 of the frame 302 and coupled to the first and second leaflet connection regions 326 and 328 to form the valve leaflets 322 (e.g., the first and second valve leaflets 346 and 348) and the reversibly sealable opening 316, as described herein. In an additional embodiment, the cover 304 can also be located over at least the inner surface 314 of the frame 302. A further embodiment includes the cover 304 located over at least the outer surface 312 and the inner surface 314. Anchoring elements (e.g., barbs) and radiopaque markers can also be included with valve 300, as described herein.

As described herein, the valve leaflets 322 can include the transition region 352 where the circumference of the cover 304 changes from a first circumference to a second circumference that is smaller than the first circumference. The transition region 352 also allows for the gap 354, as described herein, to be formed between the outer surface of the valve leaflets 322 and the inner wall of the vessel in which the valve 300 is implanted. The valve leaflets 322 can also include the concave pocket 360, as described herein. Cover 304 also includes the lip 356 that can have either a non-planar or a planar configuration, as described herein.

Frame member 318 of the valve frame 302 can also include a variety of cross-sectional shapes and dimensions. For example, cross-sectional shapes for the frame member 318 can be as described herein. In addition, the frame member 318 can have two or more cross-sectional shapes, two or more different dimensions (e.g., a greater width and depth of the frame member 318 for the first and second vertices 361 and 364 as compared to the remainder of the frame member 318).

Figure 4A:
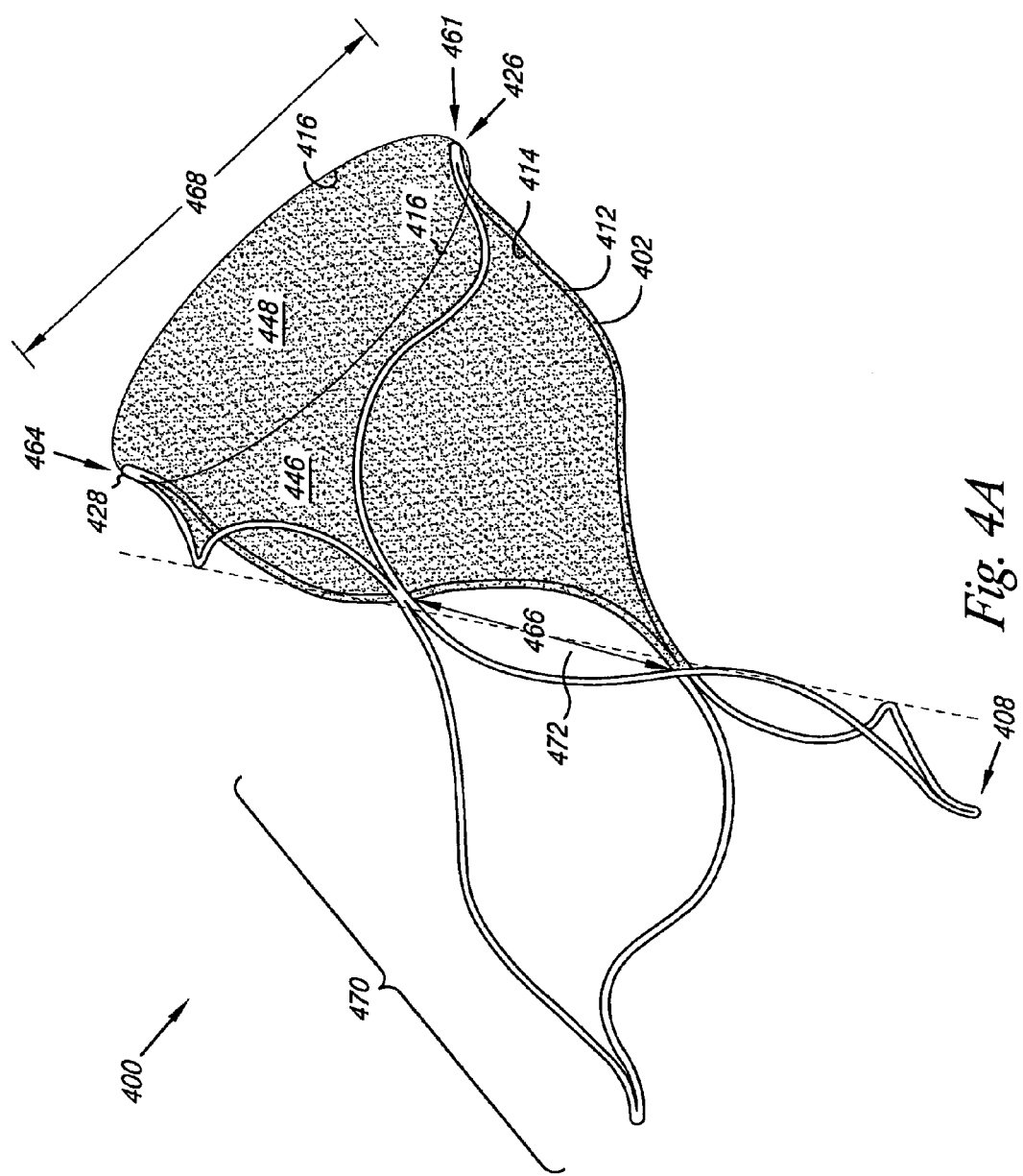
FIG. 4A illustrates an embodiment of a valve according to the present invention.
Figure 4B:
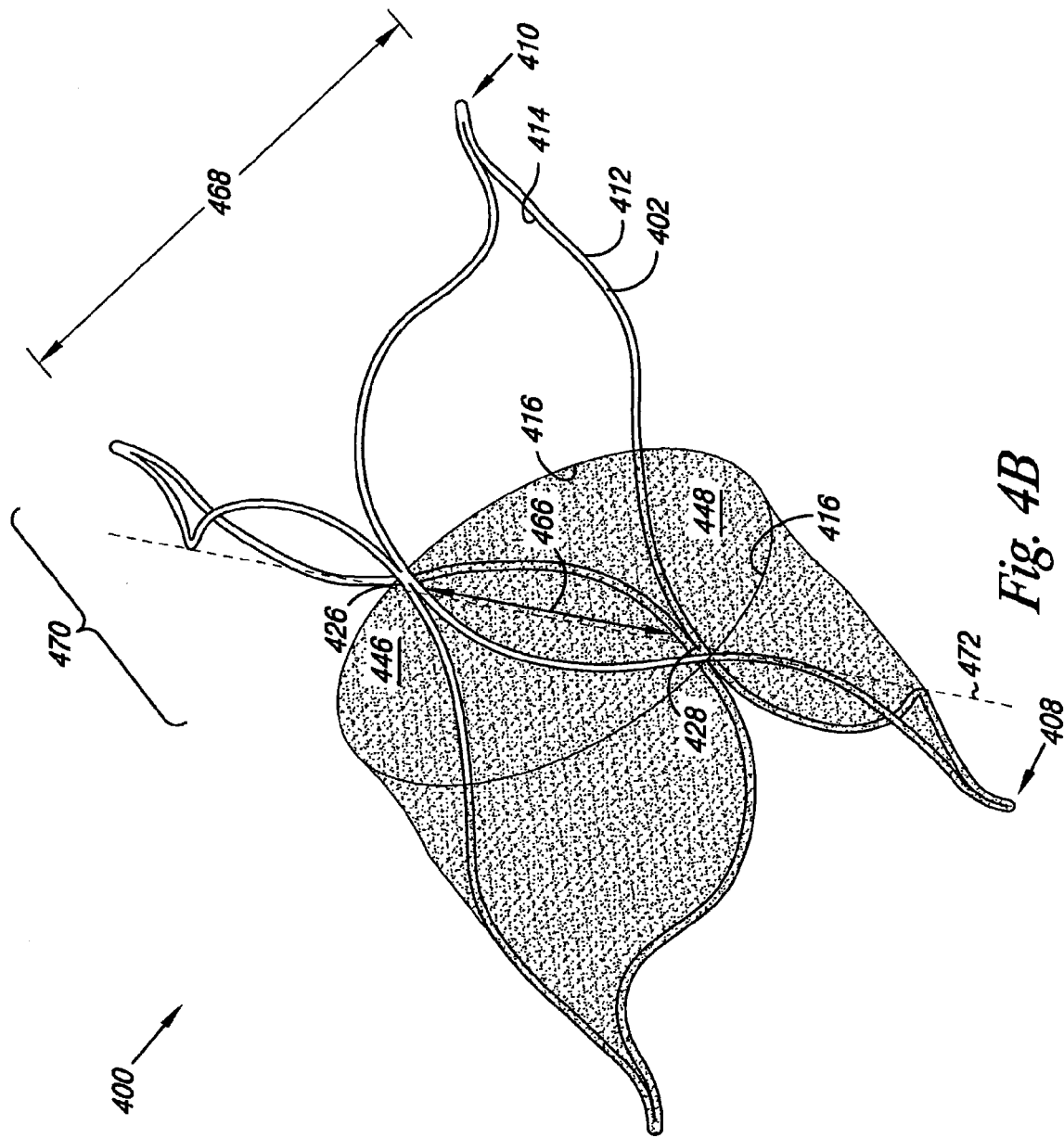
FIG. 4B illustrates an embodiment of a valve according to the present invention.

FIGS. 4A and 4B illustrate additional embodiments of the valve 400. As illustrated, the frame 402 includes an open frame configuration and the first leaflet connection region 426 and the second leaflet connection region 428, as described herein. FIGS. 4A and 4B illustrate embodiments in which the cover 404 can be positioned at different locations along the frame 402 so as to form the valve leaflets 422. For example, in FIG. 4A the leaflet connection regions 426 and 428 are located at the first vertex 461 and the second vertex 464, respectively, relative the first end 408 of the frame 402. In an additional example, FIG. 4B provides an illustration in which the leaflet connection regions 426 and 428 are positioned between the end of the frame 402 having the first vertex 461 and the second vertex 464 and the first end 408 of the frame 402.

The frame 402 can include multiple structural configurations. For example, the frame 402 can include a support frame region 470 that helps to stabilize and position the valve 400 inside a vessel. In one embodiment, FIGS. 4A and 4B provide an illustration in which the support frame region 470 extends from an axis 472 through a mid-point of the frame 402 away from the leaflet connection regions 426 and 428.

As illustrated, the outer surface 412 of the frame 402 can also provide a number of frame dimensions. For example, the outer surface 412 of the frame 402 can be viewed as defining the first frame dimension 466 at the axis 472 of the frame 402 and a second frame dimension 468 measure at either the first or second end 408, 410 of the frame 402. In one embodiment, the second frame dimension 468 can have a larger value as compared to the first frame dimension 466. Other dimensional relationships between the first and second frame dimensions 466 and 468 are also possible.

In the present embodiment, the differences in the frame 402 dimensions provide radial support members for the valve 400. In other words, radial support members of the frame 402 result from the relative shape and size of the different portions of the frame members 418. For example, as described herein the first and second frame dimensions 466, 468 can have different sizes, where the outer surface 412 of the frame 402 radially arcs from the first frame dimension 466 to the second frame dimension 468 so as to provide the radial support member of the frame 402. So, in the present example the flaring of the of the frame member 418 from the first frame dimension 466 to the second frame dimension 468 allows the frame member 418 in the region of the first and second vertex 461 and 464 to provide the radial support member.

In one embodiment, the radial support members illustrated in FIGS. 4A and 4B can serve to stabilize the valve 400 once positioned at a predetermined location as described herein. In addition, the configuration of the radial support member can allow the first frame dimension 466 and the second frame dimension 468 to more closely correspond to each other once the valve 400 has been positioned at the predetermined location.

The valve 400 can further include the cover 404, where both the frame 402 and the cover 404 can resiliently radially collapse and expand, as described herein. In the present example, the cover 404 can be located over at least the inner surface 414 of the frame 402 and coupled to the first and second leaflet connection regions 426 and 428 to form the valve leaflets 422 (e.g., the first and second valve leaflets 446 and 448) and the reversibly sealable opening 416, as described herein. In an additional embodiment, the cover 404 can also be located over at least the outer surface 412 of the frame 402. A further embodiment includes the cover 404 located over at least the outer surface 412 and the inner surface 414. Anchoring elements (e.g., barbs) and radiopaque markers can also be included with valve 400, as described herein.

Frame member 418 of the valve frame 402 can also include a variety of cross-sectional shapes and dimensions. For example, cross-sectional shapes for the frame member 418 can be as described herein. In addition, the frame member 418 can have two or more cross-sectional shapes, two or more different dimensions (e.g., a greater width and depth of the frame member 418 for one or more of the first and second vertices 461, 464 as compared to the remainder of the frame member 418).

Figure 5A:
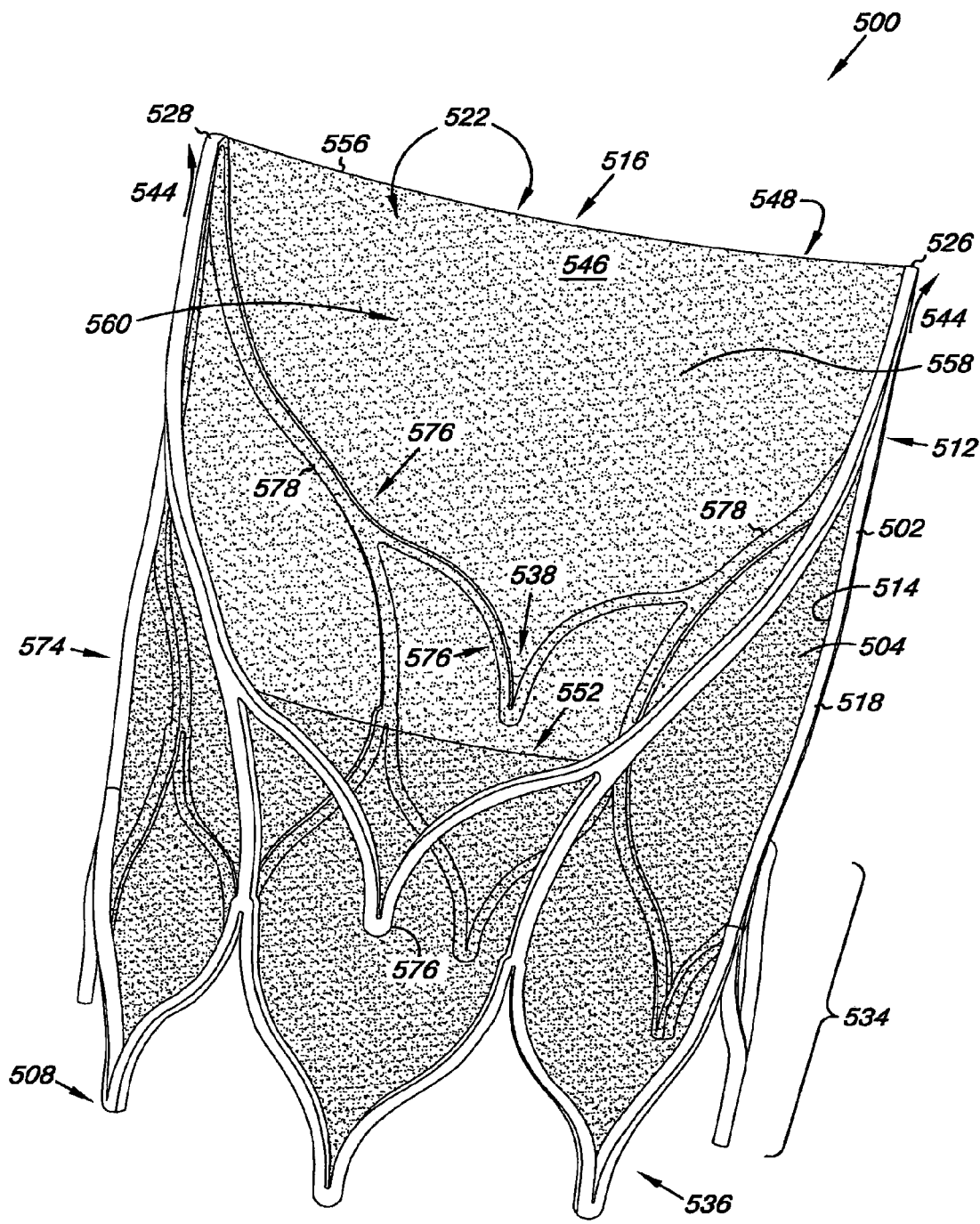
FIG. 5A illustrates an embodiment of a valve according to the present invention.
Figure 5B:
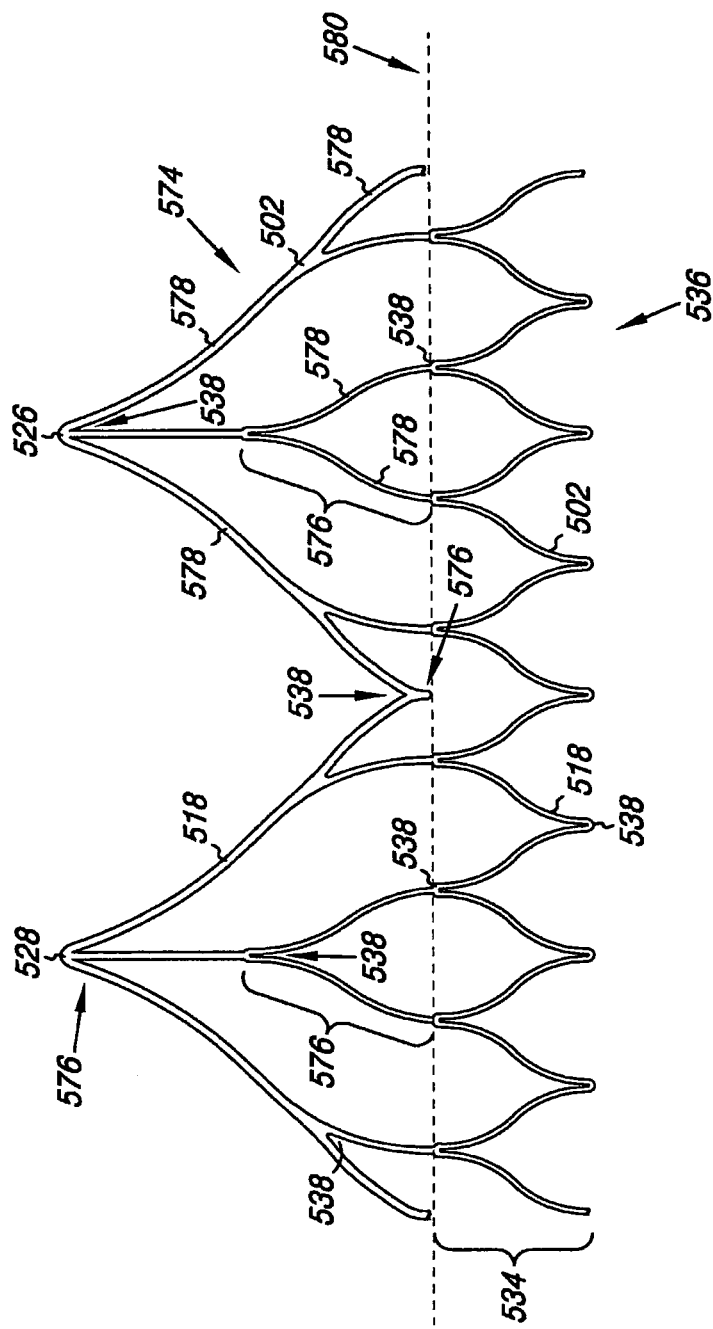
FIG. 5B illustrates an embodiment of a frame for the valve illustrated in FIG. 5A according to the present invention.

FIGS. 5A and 5B illustrate an additional embodiment of the valve 500. Valve 500 includes the cover 504 as described herein. The frame 502 of the valve 500 further includes a triple wishbone configuration 574. In one embodiment, the triple wishbone configuration 574 of the frame 502 includes a series of interconnected bifurcated members having connection points that act as spring members, as will be described herein. In one embodiment, the interconnection of these members allows for the spring force of aligned springs integrated into the frame 502 to be added in series so as to increase the spring force potential of the frame 502.

FIG. 5B provides an illustration of the triple wishbone configuration 574 for the frame 502 that has been cut to provide it in a planar view. In one embodiment, the frame member 518 in the triple wishbone configuration 574 includes a radial support member 534. As illustrated, the radial support member 534 can be in the form of a tubular ring 536 that can move radially as the valve 500 radially collapses and expands.

In one embodiment, the tubular ring 536 can provide a spring force (e.g., elastic potential energy) to counter radial compression of the frame 502 towards its uncompressed state. For example, the tubular ring 536 has a zig-zag configuration that includes corners 538 that can develop the spring force when the frame 502 is under compressed. As will be appreciated, the corners 538 can have a number of configurations, including turns defining angles and/or arcs (e.g., having a radius of curvature).

The frame 502 further includes spring members 576 interconnected with the radial support member 534. As illustrated, the spring members 576 are associated with the radial support member 534 adjacent the corners 538. For example, the spring members 576 can include extensions 578 that join the radial support member 534 adjacent the corners 538 along a common plane 580. In the present embodiment, extensions 578 join the radial support member 534 adjacent each corner 538 along the plane 580.

The spring members 576 also include corners 538 that can develop the spring force when the frame 502 is under compressed. As will be appreciated, the corners 538 can have a number of configurations, including turns defining angles and/or arcs (e.g., having a radius of curvature). In one embodiment, the corners 538 of the spring members 576 also provide the first and second leaflet connection regions 526, 528. In one embodiment, the spring members 576 interconnected with the radial support member 534 helps to stabilize the relative positions of the connection regions 526 and 528 (e.g., limit relative fluctuations of the connection regions 526 and 528).

The frame 502 in FIGS. 5A-B can be described as having a first frame end with two first frame end turns and a second frame end with a plurality of second frame end turns. The two first frame end turns form leaflet connection regions 526, 528. The plurality of second frame end turns, ring turns, and struts connecting the end turns and ring turns, form the tubular ring 536. The struts of the tubular ring 536 are of uniform length. The frame 502 further includes a plurality of frame members connecting the first frame end turns and the ring turns of the tubular ring 536. Each frame member has a body portion and two legs extending from the body portion. Each frame member is connected to one first frame end turn and either one or two of the ring turns of the tubular ring 536. For example, each leaflet connection region 526, 528 has one frame member connecting the first frame end turn and two ring turns of the tubular ring 536 (a first frame member), and two frame members connecting the first frame end turn and one ring turn of the tubular ring 536 (second frame members), with the first frame member positioned between the two second frame members. Further, one leg of each second frame member is engaged to a leg of another second frame member to form a corner 538. The frame 502 has two first frame members and four second frame members. As shown in FIG. 5B, the first frame members have a different shape than the second frame members. The frame 520 also defines a plurality of first cells, a plurality of second cells, and a plurality of third cells. The first, second, and third cells have different configurations. Each first cell is defined by one first frame member, one second frame member, and two struts of the tubular ring 536. As can be seen in FIG. 5B, one first frame member defines a portion of two first cells which are mirror images. Each second cell is defined by one first frame member and two struts of the tubular ring 536. Each third cell is defined by two second frame members and two struts of the tubular ring 536. As shown in FIG. 5B, the frame 502 defines four first cells, two second cells, and two third cells.

The frame 502 shown in FIGS. 5A-B can also be described as having two tubular rings connected one to another by connecting members. As can be seen in FIG. 5B, the common plane 580 separates the two rings, with the tubular ring above the common plane 580 being a first tubular ring, the tubular ring 536 below the common plane 580 being a second tubular ring. Each ring is formed of a plurality of struts which are interconnected by turns, e.g. corners 538. As shown in FIG. 5B, the first tubular ring has four struts and the second tubular ring 536 has sixteen struts. The struts of the first tubular ring have a same length, and the struts of the second tubular ring 536 have a same length less than the length of the struts of the first tubular ring. Each tubular ring has turns that form an end of the valve (end turns), with the second tubular ring 536 having more end turns than the first tubular ring. Turns that are not end turns can be described as ring turns. As can be seen in FIG. 5B, the connecting members of the frame are engaged only to the ring turns of the second tubular ring 536. The connecting members of the frame are further engaged either to a strut of the first tubular ring, or to an end turn of the first tubular ring. Thus the connecting members can be divided into first connecting members and second connecting members. The first connecting members connect a strut of the first tubular ring and a ring turn of the second tubular ring 536, and are shorter than second connecting members. The frame 502 has four first connecting members. The second connecting members connect an end turn of the first tubular ring and two ring turns of the second tubular ring 536. The frame 502 has two second connecting members. As shown in FIG. 5B, only first and second connecting members interconnect the first and second tubular rings.

The frame 502 can further include dimensional relationships, as described herein, which allow the frame 502 to flare radially outward relative the first end 508 of the frame. The valve 500 can further include the cover 504, where both the frame 502 and the cover 504 can resiliently radially collapse and expand, as described herein. In the present example, the cover 504 can be located over at least the inner surface 514 of the frame 502 and coupled to the first and second leaflet connection regions 526 and 528 to form the valve leaflets 522 (e.g., the first and second valve leaflets 546 and 548) and the reversibly sealable opening 516, as described herein.

The valve leaflets 522 can further include the transition region 552 where the circumference of the cover 504 changes from a first circumference to a second circumference that is smaller than the first circumference. The transition region 552 also allows for the gap, as described herein, to be formed between the outer surface of the valve leaflets 522 and the inner wall of the vessel in which the valve 500 is implanted. The valve leaflets 522 can also include the concave pocket 560, as described herein. Cover 504 also includes the lip 556 that can have either a non-planar or a planar configuration, as described herein.

Frame member 518 of the valve frame 502 can also include a variety of cross-sectional shapes and dimensions. For example, cross-sectional shapes for the frame member 518 can be as described herein. In addition, the frame member 518 can have two or more cross-sectional shapes, two or more different dimensions (e.g., a greater width and depth of the frame member 518 for the corners 538 as compared to the remainder of the frame member 518).

Figure 6:
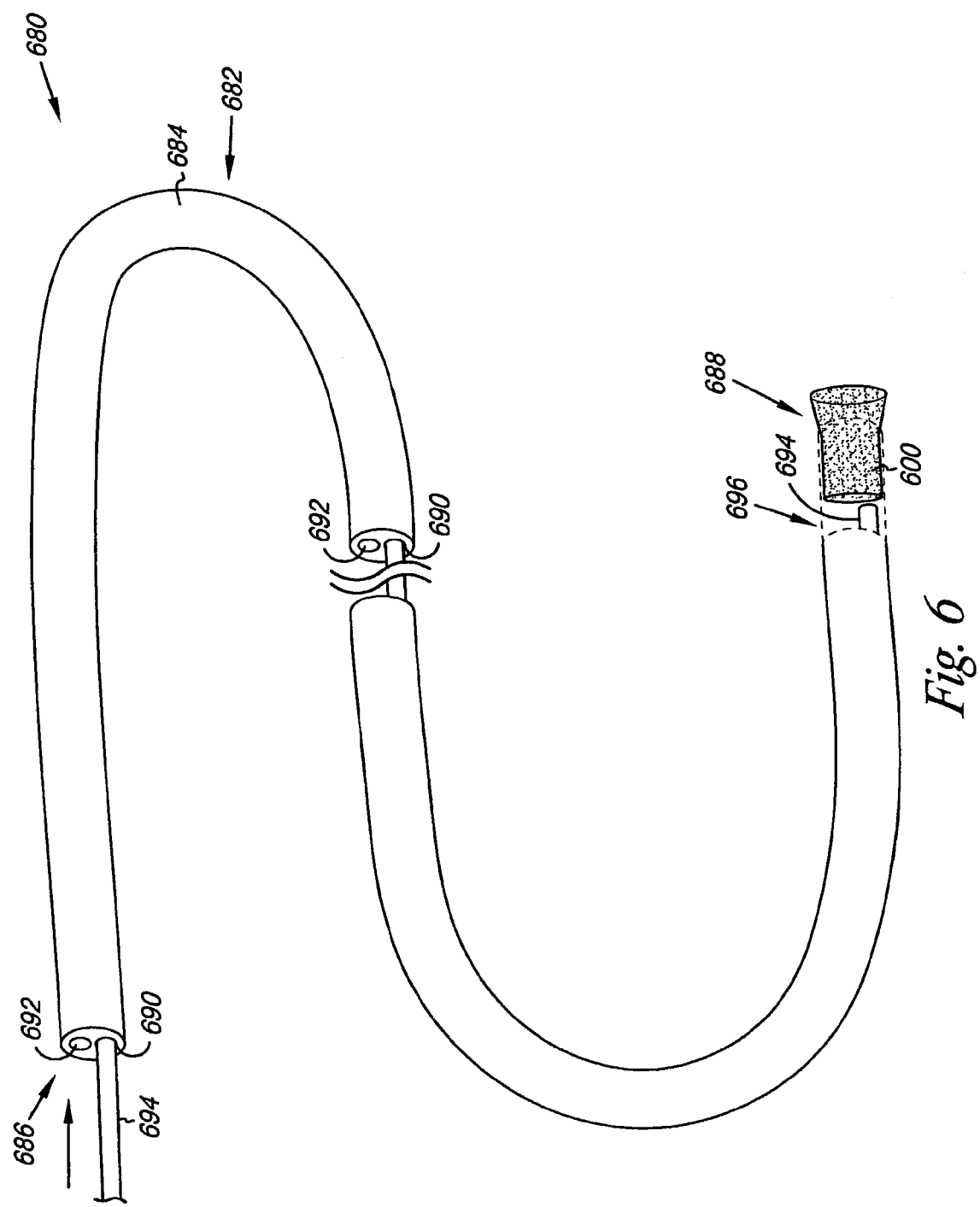
FIG. 6 illustrates an embodiment of a system that includes a valve according to the present invention.

FIG. 6 illustrates one embodiment of a system 680. System 680 includes valve 600, as described herein, reversibly joined to catheter 682. The catheter 682 includes an elongate body 684 having a proximal end 686 and a distal end 688, where valve 600 can be located between the proximal end 686 and distal end 688. The catheter 682 can further include a lumen 690 longitudinally extending to the distal end 688. In one embodiment, lumen 690 extends between proximal end 686 and distal end 688 of catheter 682. The catheter 682 can further include a guidewire lumen 692 that extends within the elongate body 684, where the guidewire lumen 692 can receive a guidewire for positioning the catheter 682 and the valve 600 within a body lumen (e.g., a vein of a patient).

The system 680 can further include a deployment shaft 694 positioned within lumen 690, and a sheath 696 positioned adjacent the distal end 688. In one embodiment, the valve 600 can be positioned at least partially within the sheath 696 and adjacent the deployment shaft 694. The deployment shaft 694 can be moved within the lumen 690 to deploy valve 600. For example, deployment shaft 694 can be used to push valve 600 from sheath 696 in deploying valve 600.

Figure 7:
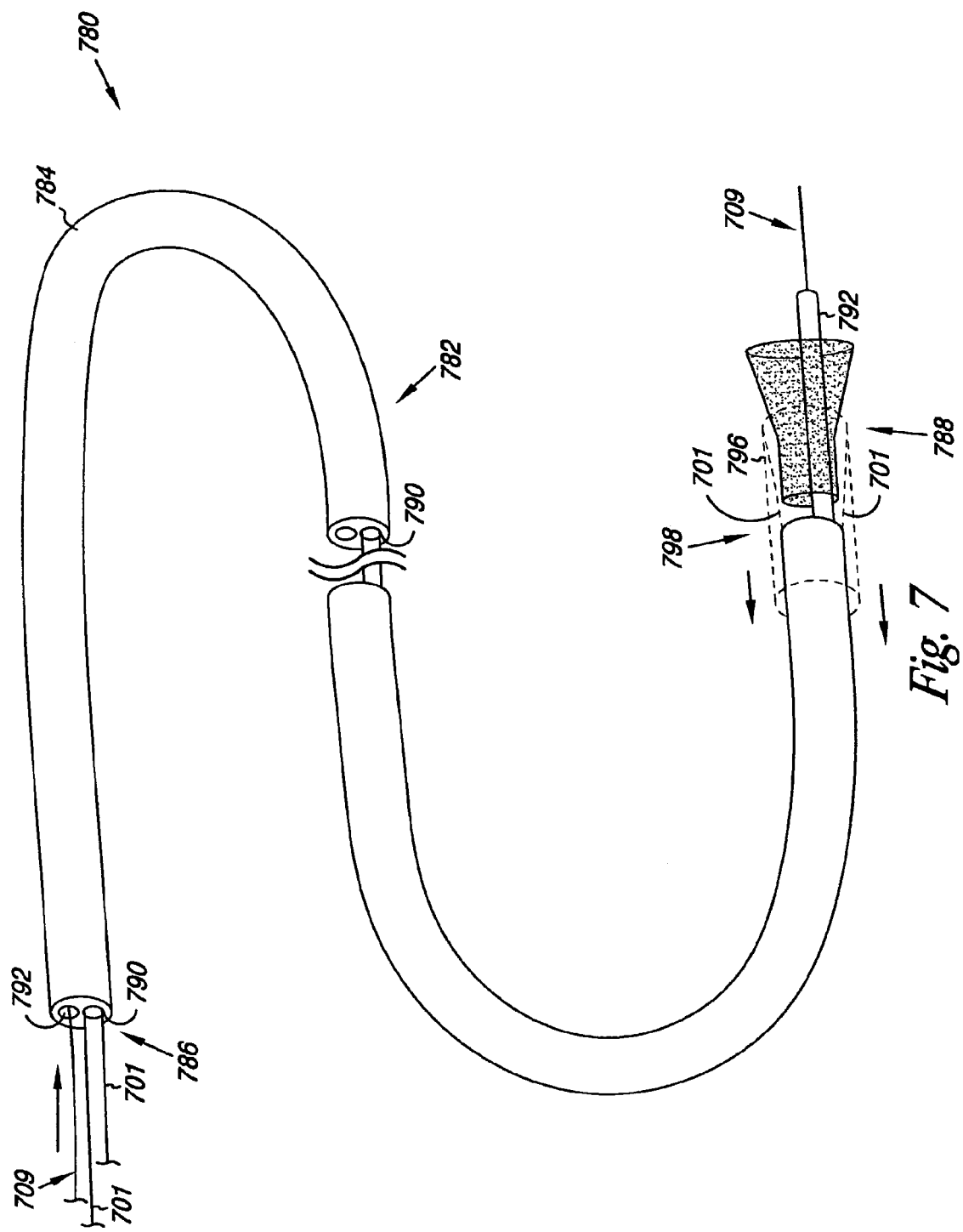
FIG. 7 illustrates an embodiment of a system that includes a valve according to the present invention.

FIG. 7 illustrates an additional embodiment of the system 780. The catheter 782 includes elongate body 784, lumen 790, a retraction system 798 and a retractable sheath 796. The retractable sheath 796 can be positioned over at least a portion of the elongate body 784, where the retractable sheath 796 can move longitudinally along the elongate body 784. The valve 700 can be positioned at least partially within the retractable sheath 796, where the retractable sheath 796 moves along the elongate body 796 to deploy the valve 700.

In one embodiment, retraction system 798 includes one or more wires 701 coupled to the retractable sheath 796, where the wires are positioned at least partially within and extend through lumen 790 in the elongate body 784. Wires of the retraction system 798 can then be used to retract the retractable sheath 796 in deploying valve 700. In one embodiment, a portion of the elongate body 784 that defines the guidewire lumen 792 extends through the lumen 706 of the valve 700 to protect the valve 700 from the movement of the guidewire 709.

Figure 8:
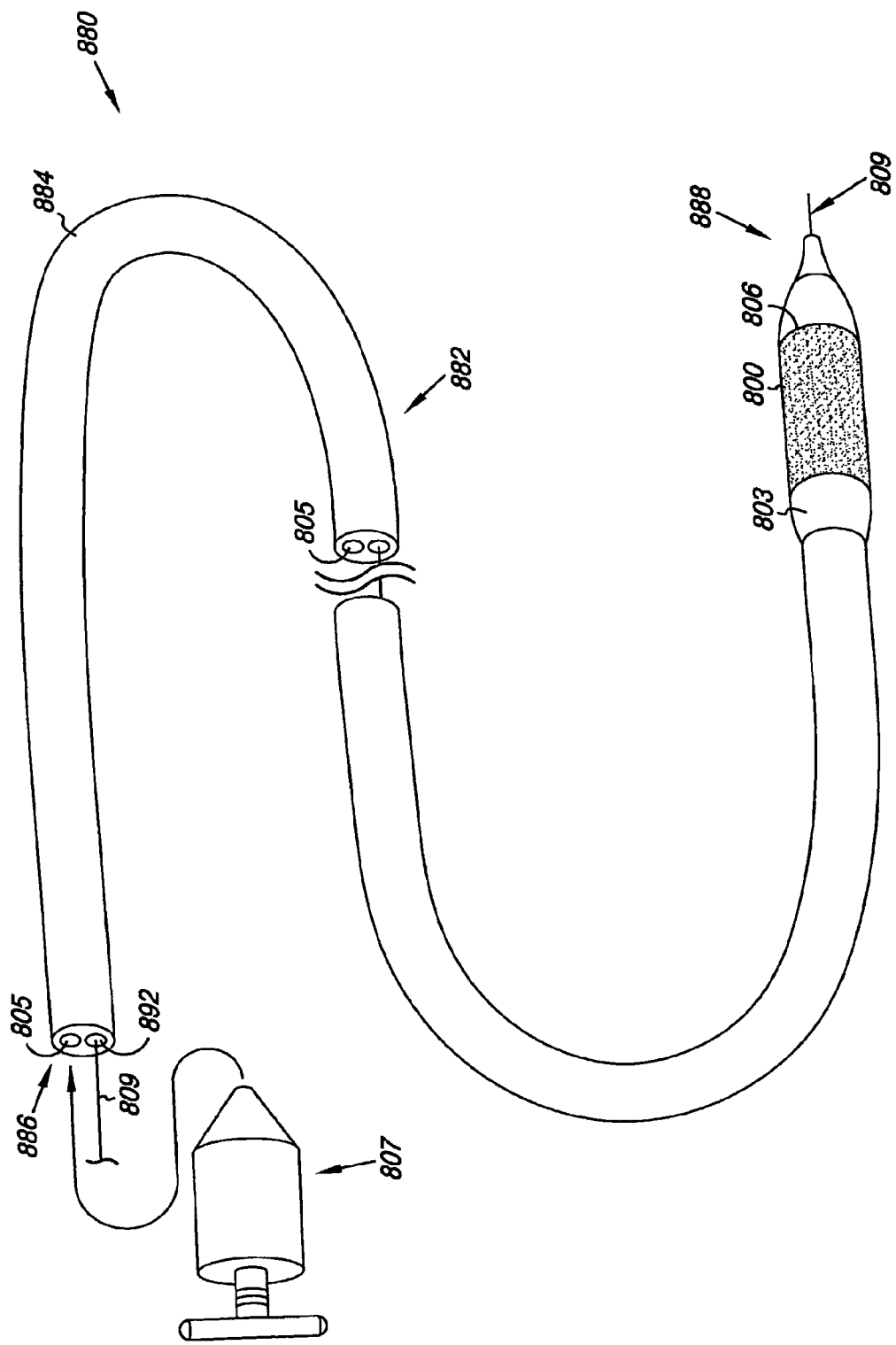
FIG. 8 illustrates an embodiment of a system that includes a valve according to the present invention.

FIG. 8 illustrates an additional embodiment of the system 880. The catheter 882 includes elongate body 884, an inflatable balloon 803 positioned adjacent the distal end 888. The elongate body 884 further includes an inflation lumen 805 longitudinally extending in the elongate body 884 of the catheter 882 from the inflatable balloon 803 to the proximal end 886. In one embodiment, an inflation pump 807 can be releasably coupled to the inflation lumen 805 and used to inflate and deflate the balloon 803.

In the present example, the inflatable balloon 803 can be at least partially positioned within the lumen 806 of the valve 800. The inflatable balloon 803 can be inflated through the lumen 805 with the inflation pump 807 to deploy the valve 800. The system 880 can further include the guidewire lumen 892 to receive a guidewire 809.

Figure 9A:
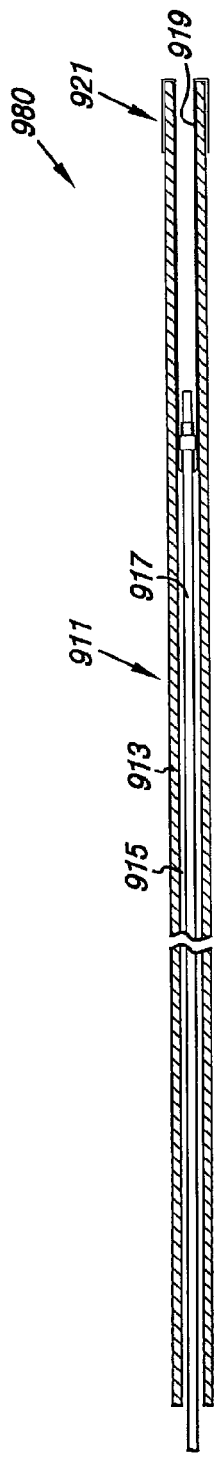
FIGS. 9A, 9B and 9C illustrate an embodiment of a system that includes a valve according to the present invention.
Figure 9B:
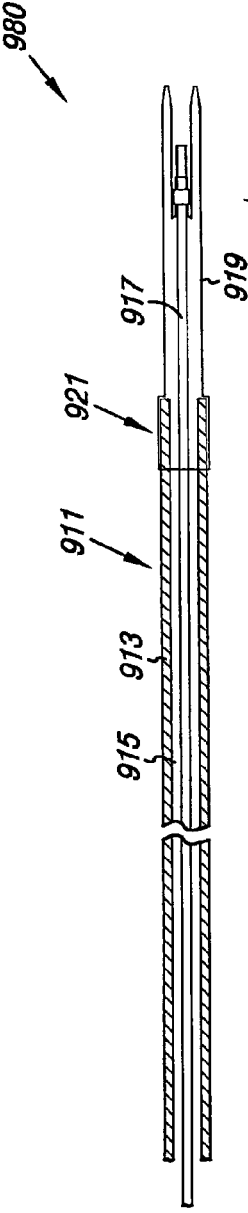
Figure 9C:
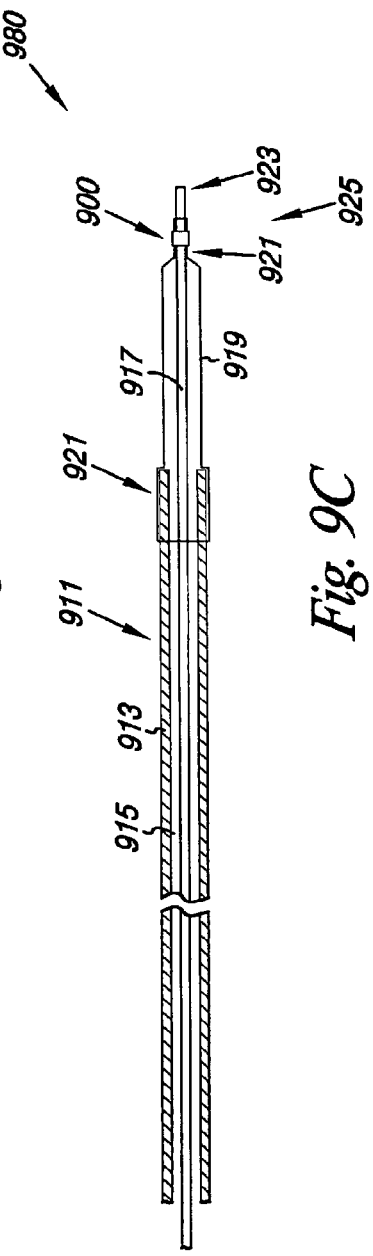

FIGS. 9A-9C illustrate an additional embodiment of the system 980. The system 980 includes a tubular sheath 911 having an elongate body 913 and a lumen 915. The system 980 further includes a delivery shaft 917 positioned within the lumen 915 of the tubular sheath 911. In one embodiment, the tubular sheath 911 and the delivery shaft 917 can move longitudinally relative each other.

System 980 also includes a flexible cover 919 between the tubular sheath 911 and the delivery shaft 917. In one embodiment, the flexible cover 919 is connected to the tubular sheath 911 and the delivery shaft 917 at a fluid tight seal 921 so as to prevent fluid from outside the system 980 entering the lumen 915. As illustrated, the valve 900 can be positioned over the delivery shaft 915 and the flexible cover 919 adjacent a distal end 923 of the delivery shaft 917.

In one embodiment, the tubular sheath 911, the delivery shaft 917 and the flexible cover 919 can each be formed from a number of different materials. For the tubular sheath examples include, but are not limited to materials selected from one or more of ePTFE, PTFE, PE, PET, silicone, and polyurethanes. For the delivery shaft 917 examples include, but are not limited to, those selected from a metal, a metal alloy, and/or a polymer. Examples include, but are not limited one or more of ePTFE, PTFE, PE, nylons, PET, silicone, polyurethanes, and stainless steel (e.g., 316L).

In addition, the delivery shaft 917 can also include a configuration that imparts sufficient column rigidity to allow it to be pushed and/or pulled through the lumen 915. For example, the delivery shaft 917 can be formed with reinforcing members bound within the body of the delivery shaft 917 (e.g., an elongate braid of stainless steel co-extruded with a polymer). For the flexible cover 919 examples include, but are not limited to, materials selected from one or more of ePTFE, PTFE, PE, PET, nylons, and polyurethanes. As will be appreciated, other materials and configurations for forming the tubular sheath 911, the delivery shaft 917 and the flexible cover 919 are also possible.

As illustrated in FIGS. 9A-9C, the valve 900 can be held in the same relative location 925 as it is being deployed. As illustrated in FIG. 9A, the valve 900, a portion of the flexible cover 919 and the delivery shaft 917 can be positioned within the lumen 915 of the tubular sheath 911. In one embodiment, the configuration illustrated in FIG. 9A allows the valve 900 to be delivered in its compressed state to a predetermined location in the lumen of the body. Once at the predetermined location, the sheath 911 can then be moved relative the delivery shaft 917. FIG. 9B illustrates a situation where the sheath 911 has been pulled over the valve 900 location 925 and at least partially over the delivery shaft 917.

As illustrated, the flexible cover 919 has a tubular configuration that folds back inside of itself (i.e., its lumen) as the tubular sheath 911 is drawn over the valve 900 and the delivery shaft 917. In one embodiment, the lumen 915 of the sheath 911 can contain a lubricating fluid (e.g., saline) to allow the flexible cover 919 to more easily pass over itself as illustrated. As the tubular sheath 911 continues to be pulled back relative the delivery shaft 917 until the valve 900 is released, as illustrated in FIG. 9C. In one embodiment, the valve 900 can include a self-expanding frame that allows the valve 900 to deploy at location 925 once released.

The embodiments of the present invention further include methods for forming the valve of the present invention, as described herein. For example, the method of forming the valve can include forming the frame having the leaflet connection regions, as described. The method can include providing the radial support member, or members, on the frame for the leaflet connection regions. As described herein, the radial support member can include the tubular rings and/or the radial flares imparted into the leaflet connection regions. The method also includes providing the cover on the frame, where connecting the cover to the leaflet connection regions provides at least the first leaflet and the second leaflet of the valve having surfaces defining the reversibly sealable opening for unidirectional flow of a liquid through the valve.

In an additional example, the valve can be reversibly joined to the catheter, which can include a process of altering the shape of the valve from a first shape, for example an expanded state, to the compressed state, as described herein. For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In an another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present invention may be used to replace an incompetent venous valve and help to decrease backflow of blood in the venous system of the legs.

In one embodiment, the method of replacing, supplementing, and/or augmenting a valve structure can include positioning at least part of the catheter including the valve at a predetermined location within the lumen of a body. For example, the predetermined location can include a position within a body lumen of a venous system of a patient, such as a vein of a leg.

In one embodiment, positioning the catheter that includes the valve within the body lumen of a venous system includes introducing the catheter into the venous system of the patient using minimally invasive percutaneous, transluminal catheter based delivery system, as is known in the art. For example, a guidewire can be positioned within a body lumen of a patient that includes the predetermined location. The catheter, including valve, as described herein, can be positioned over the guidewire and the catheter advanced so as to position the valve at or adjacent the predetermined location.

As described herein, the position of the one or more radiopaque markers can be selected so as to provide information on the position, location and orientation (e.g., axial, directional, and/or clocking position) of the valve during its implantation. For example, radiopaque markers can be configured radially and longitudinally on predetermined portions of the valve frame and/or the elongate body of the catheter to indicate not only a longitudinal position, but also a radial position of the valve leaflets and the valve frame (referred to as a clock position). In one embodiment, the radiopaque markers are configures to provide radiographic images that indicate the relative radial position of the valve and valve leaflets on the catheter.

Figure 10A:
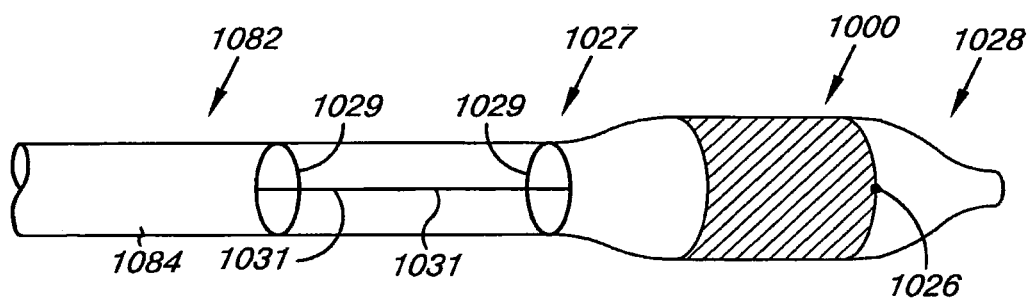
FIGS. 10A, 10B and 10C illustrate an embodiment of a system that includes a valve and a catheter having radiopaque markers according to the present invention.
Figure 10B:
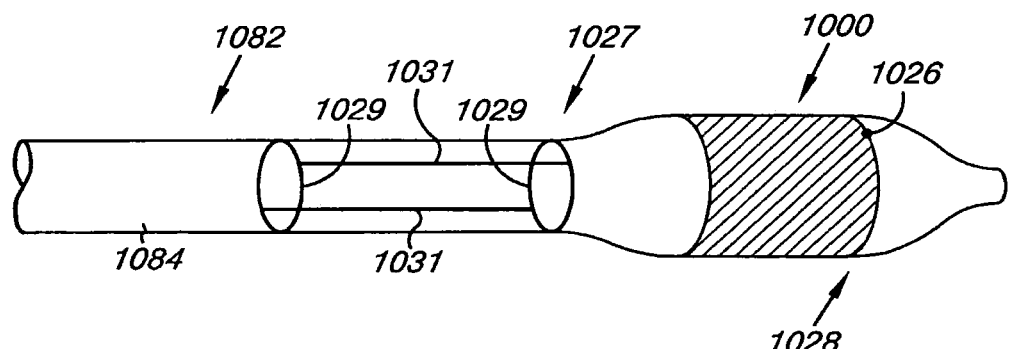
Figure 10C:
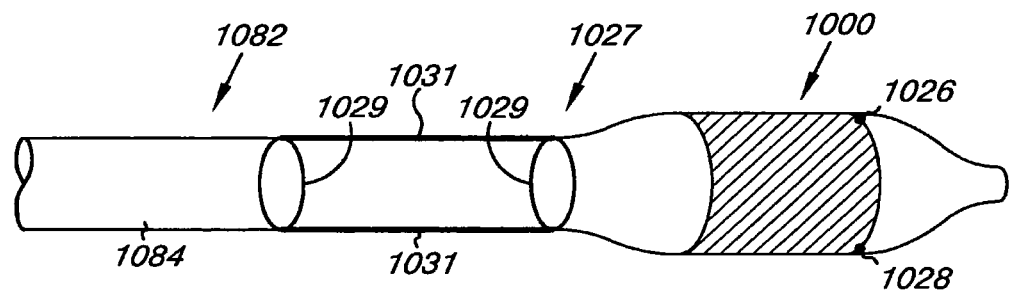

FIGS. 10A-10C provide an illustration of the radiopaque markers 1027 associated with the elongate body 1084 of the catheter 1082. As illustrated, the radiopaque markers 1027 include a radial component 1029 and a longitudinal component 1031. Depending upon the radial position of the catheter 1082, the radiopaque markers 1027 can provide a different and distinguishable radiographic image. For example, in a first position 1033 illustrated in FIG. 10A the longitudinal component 1031 of the radiopaque markers 1027 are aligned so as to overlap. As the catheter 1082 is rotated, as illustrated in FIGS. 10B and 10C, the radiographic image of the radial component 1029 and/or longitudinal component 1031 of the radiopaque markers 1027 change.

The change in the relationship of the radial and longitudinal components 1029, 1031 as the catheter 1082 is rotated allows for the relative position of the valve, valve frame and valve leaflets to be determined from the radiographic image. For example, the relative position of the first and second leaflet connection regions 1026, 1028 could be aligned with longitudinal component 1031 of the radiopaque markers 1027. This would allow the clock position for the valve 1000 to be determined so that the valve can be positioned in a more natural orientation relative the compressive forces the valve will experience in situ. In other words, the allowing for clocking of the valve 1000 as described herein allows the valve to be radially positioned in same orientation as native valve that it's replacing and/or augmenting.

As will be appreciated, other relative relationships between the radiopaque markers 1027 and the position of the valve 1000 on the catheter 1082 are possible. So, embodiments of the present invention should not be limited to the present example. For example, additional radiopaque markers 1027 on the valve 1000 could be used either alone or in combination with radiopaque markers 1027 on the catheter 1082 to help in positioning the valve 1000 within a lumen.

The valve can be deployed from the catheter at the predetermined location in a number of ways, as described herein. In one embodiment, valve of the present invention can be deployed and placed in a number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As described herein, the valve can be deployed from the catheter in a number of ways. For example, the catheter can include the retractable sheath in which valve can be at least partially housed, as described herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as described herein. Valve can be deployed by moving the deployment shaft through the catheter to deploy valve from the sheath, where the valve self-expands to be positioned at the predetermined location. In an additional embodiment, the valve can be deployed through the use of an inflatable balloon.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

In addition, the use of both the radial support member and/or the support frame region of the valve can provide a self centering aspect to valve within a body lumen. In one embodiment, the self centering aspect resulting from the radial support member and/or the support frame region may allow valve to maintain a substantially coaxial alignment with the body lumen (e.g., such as a vein) as valve leaflets deflect between the open and closed configurations so as to better seal the reversible opening when valve is closed.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the frame 102 and/or the cover 104 can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A valve having a first end and a second end, the valve comprising:
    a frame, the frame comprising:
        a first frame end having only two first frame end turns, the two first frame end turns forming the first end of the valve; and
        a second frame end comprising a plurality of second frame end turns, the plurality of second frame end turns forming the second end of the valve, the second end of the valve having more end turns than the first end of the valve, the plurality of second frame end turns forming a part of a tubular ring having a serpentine configuration, the tubular ring further comprising ring turns connected to the second frame end turns by struts;
        a plurality of frame members, each frame member connected to one first frame end turn and one or two of the ring turns, each ring turn connected to a single frame member, each first frame end turn having three frame members engaged thereto; and
    a plurality of valve leaflets engaged to the frame.

2. The valve of claim 1, each of the plurality of frame members having a body portion and two legs, each first frame end turn engaged to the body portion of the three frame members, and each ring turn engaged to a single leg of one of the three frame members.

3. The valve of claim 2, the plurality of frame members including first frame members having a first shape and second frame members having a second shape different than the first shape.

4. The valve of claim 3, the frame having two first frame members and four second frame members.

5. The valve of claim 4, each leg of a first frame member engaged to a ring turn of the tubular ring, a first leg of each second frame member engaged to a ring turn of the tubular ring, and a second leg of a second frame member engaged to a second leg of another second frame member.

6. The valve of claim 3, each first frame member being between two second frame members.

7. The valve of claim 1, the struts of the tubular ring having a same length.

8. The valve of claim 1, the frame defining:
    a plurality of first cells each having a first configuration;
    a plurality of second cells each having a second configuration; and
    a plurality of third cells each having a third configuration;
    the first, second, and third configurations being different configurations.

9. The valve of claim 1, the plurality of leaflets comprising a first valve leaflet and a second valve leaflet, the valve further comprising:
    a cover comprising
        a first cover end, the first cover end attached to the tubular ring;
        a second cover end region, the second cover end region forming the first valve leaflet and the second valve leaflet; and
        a second cover end, the second cover end engaged to the two first frame end turns.

10. The valve of claim 1, wherein the tubular ring has an uniform longitudinal length.

11. The valve of claim 1, wherein there is an equal number of second frame end turns and ring turns.

12. A valve comprising:
    a frame comprising:
        a first tubular ring having a serpentine configuration comprising first struts of a same first length, the first struts interconnected by turns, wherein two of the turns are first end turns that form a first end of the valve;
        a second tubular ring positioned a longitudinal distance from the first tubular ring, the second tubular ring having a serpentine configuration comprising second struts of a same second length, the second length being less than the first length, the second struts interconnected by turns, the turns including second end turns and ring turns, the second end turns forming a first end of the tubular ring and a second end of the valve, the ring turns forming a second end of the tubular ring; and frame members interconnecting the first and second tubular rings, the frame members engaged only to the ring turns of the second tubular ring, each ring turn of the second tubular ring connected to a frame member, the frame members including first frame members and second frame members, the first frame members having a greater longitudinal extent than the second frame members;

valve leaflets engaged to the frame.

13. The valve of claim 12, wherein the second tubular ring has a greater wavelength than the first tubular ring.

14. The valve of claim 12, the second end of the valve having more turns than the first end of the valve.

15. The valve of claim 12, each first frame member connecting a first end turn and two ring turns.

16. The valve of claim 12, each second frame member connecting one first strut and one ring turn.

17. The valve of claim 12, wherein only first and second frame members interconnect the first and second tubular rings.

* * * * *